United States Patent [19]

Almquist et al.

[11] Patent Number: 4,705,778

[45] Date of Patent: Nov. 10, 1987

[54] ORALLY ACTIVE LHRH ANALOGS

[75] Inventors: Ronald G. Almquist, Palo Alto; Cris M. Olsen, Felton, both of Calif.

[73] Assignee: SRI International, Menlo Park, Calif.

[21] Appl. No.: 790,031

[22] Filed: Oct. 22, 1985

[51] Int. Cl.[4] .................... A61K 37/43; C07K 7/20
[52] U.S. Cl. ....................... 514/15; 514/800; 530/313
[58] Field of Search .............. 514/800; 530/313; 514/15

[56] References Cited

U.S. PATENT DOCUMENTS

| | | | |
|---|---|---|---|
| Re. 30,731 | 9/1981 | Hudson et al. | 514/15 |
| 3,992,365 | 11/1976 | Beddell et al. | 514/800 |
| 4,100,274 | 7/1978 | Dutta et al. | 514/800 |
| 4,124,703 | 11/1978 | Dutta et al. | 514/800 |
| 4,341,767 | 7/1982 | Nestor et al. | 514/15 |
| 4,410,514 | 10/1983 | Vale, Jr. et al. | 514/15 |
| 4,431,635 | 2/1984 | Coy et al. | 514/15 |
| 4,444,759 | 2/1984 | Rivier et al. | 514/15 |
| 4,490,291 | 12/1984 | Fujino | 530/313 |
| 4,565,804 | 1/1986 | Rivier et al. | 514/15 |
| 4,569,927 | 2/1986 | Rivier et al. | 514/15 |

FOREIGN PATENT DOCUMENTS

| | | |
|---|---|---|
| 2811267 | 9/1978 | Fed. Rep. of Germany. |
| 84/03507 | 4/1983 | PCT Int'l Appl.. |
| 1587809 | 4/1981 | United Kingdom. |

OTHER PUBLICATIONS

*Biochem Biophys Res Comm* (1979). 86,4:1266, by Channabasavaiah et al.
*J Med Chem* (1975) 18,12:1247 by Beattie et al.
*J Med Chem* (1974) 17,9:1016 by Rees et al.
*Ann Clin Res* (1978) 10:139, of Coy and Schally.
*Tetrahedron Letters* (1982) 23,25:2533–2534.
*J Med Chem* (1980) 23:1392.
*LHRH and Its Analogs, Contraceptive and Therapeutic Applications*, B. H. Vickery et al, Eds, MTP Press Limited, Lancaster, PA, 1984.

Primary Examiner—Delbert R. Phillips
Attorney, Agent, or Firm—Ciotti & Murashige, Irell & Manella

[57] ABSTRACT

Incorporation of a ketomethylene or a hydroxyethylene group in place of the amide linking group between the Pro[9] and Gly[10] residues of LHRH and its analogs improves the oral activity of LHRH or its analogs.

18 Claims, No Drawings

ORALLY ACTIVE LHRH ANALOGS

ORIGIN OF THE INVENTION

This invention was made with government support under Grant No. 15258 awarded by the National Institutes of Health. The United States Government has certain rights in this invention.

FIELD OF THE INVENTION

This invention relates to peptides which are analogs of the decapeptide luteinizing hormone-releasing hormone (LHRH) and their preparation. More particularly, the present invention is directed to 9,10-position-modified analogs of LHRH which exhibit increased oral activity.

BACKGROUND OF THE INVENTION

Luteinizing hormone-releasing hormone is the decapeptide pGlu-His-Trp-Ser-Tyr-Gly-Leu-Arg-Pro-Gly-$NH_2$ (LHRH). It binds to specific membrane-bound receptors on the gonadotropes and stimulates them to secrete luteinizing hormone (LH) and follicle-stimulating hormone (FSH). (R. N. Clayton and K. J. Catt, *Endocr Rev* (1981) 2: 186.)

Peptides are compounds which contain two or more amino acids in which the carboxyl group of one acid is linked to the amino group of the other acid as an amide. The formula for LHRH, as represented above, is in accordance with conventional representations of peptides where the amino terminus appears to the left and the carboxyl terminus to the right. The position of the various amino acid residues is indicated by numbering from left to right. In the case of LHRH, the hydroxyl portion of the carboxylic acid of the 10-position amino acid has been replaced with an amino group to give an amide function.

Over fifteen hundred agonist and antagonist analogs of LHRH in which one or more of the peptide amino acid residues are replaced or modified have been synthesized. An excellent review of much of the work is given in the book *LHRH and Its Analogs, Contraceptive and Therapeutic Applications*, B. H. Vickery et al, eds, MTP Press Limited, Lancaster, PA, 1984 ("Vickery et al").

As set out by J. J. Nestor, Jr. in chapter 1 of that book, a range of agonist analogs of LHRH have been prepared, including nonapeptide alkyl amides such as [$Pro^9$-NHEt] LHRH and buserelin ([D-Ser(t-Bu)$^6$, $Pro^9$-NHEt] LHRH) and material incorporating an Aza-Gly(NHNHCO-) in position 10. In addition, modification in position 6, especially by adding hydrophobic groups, has been shown to enhance activity. LHRH and its agonist analogs have been proposed for use in male and female contraception, treatment of precocious puberty, endometriosis, first trimester pregnancy interruption, and the treatment of breast and prostate tumors.

As pointed out by M. V. Nekola et al in chapter 10 of the Vickery et al text, LHRH antagonists have been synthesized having substitution in one or more of the 1, 2, 3, 6, and 10 positions. Such materials can be used to prevent the release of the LH and FSH gonadotropins so as to inhibit ovulation and terminate pregnancy and to produce a male contraceptive effect by interrupting spermatogenesis. These antagonists are useful as well in treating breast, prostate, and other reproductive tissue cancers, nonreproductive organ tumors, and ectopic tumors, particularly those secreting chorionic gonadotropin. Other uses for LHRH antagonist analogs include treatment of endometriosis and the symptoms of menopause.

The art surrounding LHRH, its analogs, and their activities is substantial. In addition to the collection of papers on the subject in Vickery et al, representative articles and patents include: U.S. Pat. No. 4,444,759 of Rivier et al, which discloses LHRH analogs modified at the 1, 2, 5, 6, and/or 7 positions and carrying a Gly—$NH_2$, NH—$CH_2$—$CH_3$ or D—Ala—$NH_2$ at the 10 position; U.S. Pat. No. 4,341,767 of Nestor et al, which shows LHRH antagonists having the LHRH structure substituted at the 1, 2, 3 and/or 6 positions with a glycinamide or a —HN—R' (wherein R' is an alkyl or the like) at the 10 position; U.S. Pat. No. 4,410,514 of Vale et al showing a decapeptide similar to LHRH which promotes fish spawning and which has variable amino acid residues at its 6 and 10 positions; U.S. Pat. No. 4,431,635 of Coy et al, which shows LHRH antagonists having variable amino acid residues at the 1, 2, and 6 positions and optionally at the 3 and 10 positions; *Biochem Biophys Res Comm* (1979) 86, 4: 1266 by Channabasavaiah et al, which discloses 1, 2, 3, 6-modified analogs of LHRH and their ability to inhibit ovulation in rodents; *J Med Chem* (1974) 17, 9: 1016, by Rees et al, which shows a variety of 2-modified analogs of LHRH and their agonist and antagonist activity; *J Med Chem* (1975) 18, 12: 1247, of Beattie et al, which shows a group of 2, 6-modified analogs; and *Ann Clin Res* (1978) 10: 139, of Coy and Schally, which shows that LHRH analogs wherein the position 10 glycine-amide residue is replaced with an alkyl amide are active in LH release.

Two other references that are co-authored by the present inventor are *Tetrahedron Letters* (1982) 23, 25: 2533–2534, which concerns synthesis of ketomethylene analogs of dipeptides; and *J Med Chem* (1980) 23: 1392, which is related to a ketomethylene analog of a tripeptide inhibitor of angiotensin. Neither of these last two references discloses LHRH analogs or discusses their activity.

Other references which mention ketomethylene substitution of peptides are U.S. Pat. No. Re. 30,731, of Hudson et al, reissued on Sep. 1, 1981, British Pat. No. 1,587,809, and German O.L.S. No. 2811267 of National Research Development Corporation, London, and PCT WO84/03507 of Ferring A.B.

One drawback to the use of LHRH and its agonist and antagonist analogs has been their low activity following oral administration. Oral doses are often as much as 1,000 times or 10,000 times less active than the parenteral (subcutaneous injection) dose. Oral doses are often much less active (such as 100 times less active) than nasally administered material. By the present invention, a structural modification in the chain of LHRH and its analogs is provided which substantially increases their oral activity.

STATEMENT OF THE INVENTION

In accord with this invention, the oral activity of LHRH and its analogs is increased by replacing the $Pro^9$-$Gly^{10}$ amide linkage with a ketomethylene group

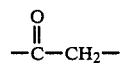

or a reduced ketomethylene group, i.e., a hydroxy-ethylene group $$-\overset{\underset{\displaystyle |}{OH}}{CH}-CH_2-.$$

This modification can be applied to LHRH to yield the peptides Pro[9]-KmGly[10] LHRH and Pro[9]-H$_2$KmGly[10] LHRH. It can, as well, be applied to the various analogs of LHRH, both agonists and antagonists, to increase their oral activity.

In additional aspects, this invention provides the Pro-KmGly and Pro-H$_2$KmGly precursors which can be incorporated to give the LHRH analogs of this invention as well as a ketal version of Pro-KmGly, referred to herein as Pro-KamGly, which can be incorporated into intermediates and which is ultimately converted to the Pro-KmGly structure.

In yet further aspects, the invention provides pharmaceutical preparations that incorporate the Pro-KmGly and Pro-H$_2$KmGly LHRH analogs.

DETAILED DESCRIPTION OF THE INVENTION

Abbreviations and Nomenclature

Certain abbreviations are used throughout the application. The abbreviations for the individual amino acid residues present in the peptide chains are conventional and are based on the trivial names of the amino acids, as shown in Table 1.

TABLE 1

| Abbreviation | Amino Acid |
|---|---|
| Ala | alanine |
| Abu | 2-aminobutyric acid |
| Arg | arginine |
| Asp | aspartic acid |
| h-Arg(Et$_2$) | diethylguanidino-substituted arginine |
| Ac—Ala, etc | N—acylalanine, etc |
| Bia | Structure 1 in footnote, where X = NH, Y = H |
| Boa | Structure 1 in footnote, where X = O, Y = H |
| Bta | Structure 1 in footnote, where X = S, Y = H |
| pBr—Phe | p-bromophenylalanine |
| Chg | 2-cyclohexylglycine |
| Cys | cysteine |
| pCl—Phe | p-chlorophenylalanine |
| Dca | dicyclohexylmethylalanine |
| Dcb | Structure 1 in footnote, where X = NH, Y = CH$_3$ |
| Dmb | Structure 1 in footnote, where X = NH, Y = Cl |
| pF—Phe | p-fluorophenylalanine |
| pGlu | pyroglutamic acid |
| Gly | glycine |
| His | histidine |
| Bzl—His | benzylhistidine |
| Ile | isoleucine |
| Leu | leucine |
| Lys | lysine |
| Met | methionine |
| NVa | norvaline |
| Nal or Nal (2) | β-naphthyl alanine |
| Nle or N—Leu | norleucine |
| N—Me—Leu | N—methylleucine |
| 3-Pal | 3-pyridylalanine |
| Ac—Pro | N—acylproline |
| Pro | proline |
| Phg | C—phenylglycine |
| Phe | phenylalanine |
| Me$_5$—Phe | 3-(2,3,4,5,6-pentamethylphenylalanine |
| Orn | ornithine |
| Ser | serine |

TABLE 1-continued

| Abbreviation | Amino Acid |
|---|---|
| t-bu-Ser | tertiary butylserine |
| Trp | tryptophan |
| Tyr | tyrosine |
| Thr | threonine |
| Tmp | 2,4,5-trimethylphenylalanine |
| Ac—Trp | N—acyltryptophan |
| Val | valine |

STRUCTURE 1

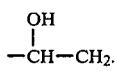

(See chapter 3, page 26, of Vickery, et al, Eds.)
Generally, substituted amino acids are abbreviated with the abbreviation for the substituent first followed by an abbreviation for the base acid.

Other abbreviations for chemicals and groups used herein include those set forth in Table 2.

TABLE 2

| Abbreviation | Chemical or Group |
|---|---|
| —NHEt | —NH—CH$_2$—CH$_3$ |
| DCC | dicyclohexylcarbodiimide |
| —Ac | acyl |
| —t-Bu | tertiary butyl |
| Bz | benzoyl |
| Cbz | benzyloxycarbonyl |
| Bzl | benzyl |
| Ts | p-toluenesulfonyl |
| DIEA | diisopropylethylamine |
| Boc | t-butoxycarbonyl |
| Fmoc | 9-fluorenylmethoxycarbonyl |

Two abbreviations of particular importance are Km for "ketomethylene"

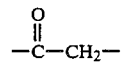

and H$_2$Km for "dihydroketomethylene"

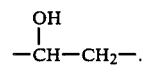

Typical uses would be in the context of [Pro[9]-KmGly[10]] LHRH to represent LHRH in which the amide between the 9 and 10 groups has been replaced by a ketomethylene (—CO—CH$_2$—) and [Pro[9]-H$_2$KmGly[10]]LHRH to represent LHRH in which the 9-10 amide group has been replaced by a —CHOH—CH$_2$—.

A related abbreviation is "Kam" for ketalmethylene or —C(OCH$_2$)$_2$CH$_2$—. This abbreviation is used in the context of, for example, Pro-KamGly to represent a proline-glycine unit joined through a —C(OCH$_2$)$_2$CH$_2$— instead of a —CONH—.

The LHRH Analogs

The LHRH polypeptide analog materials of this invention include Pro[9]-KmGly[10]LHRH and Pro[9]-H$_2$KmGly[10]LHRH, i.e, pGlu-His-Trp-Ser-Tyr-Gly-Leu-Arg-Pro-KmGly-NH$_2$ and pGlu-His-Trp-Ser-Tyr-Gly-Leu-Arg-Pro-H$_2$KmGly-NH$_2$, as well as materials where one or more of the first eight amino acid residues are replaced or substituted, as is known in the art.

Representative modifications of the first eight amino acids include: At position 1 replacing L-pGlu with $R_1$ wherein $R_1$ is D-pGlu, Ac-D or -L-Pro, Ac-L-Trp, substituted D-Ala, Ac-D-Phe, or Ac-phalo-D-Phe, as shown in U.S. Pat. No. 4,341,767; D-Nal or Ac-D-Nal, as shown in U.S. Pat. No. 4,444,759; Gly, L-Ala, D-Ala, D-Trp, D-Phe, or substituted D-Phe, each having the possibility of being additionally substituted with an alkanoyl, a HOOC—$(CH_2)_n$—CO— where n is 2 to 6, a benzoyl or the acyl portion of glycine or a like D or L amino acid as set forth in U.S. Pat. No. 4,431,635; Ac-L-Pro, Ac-phalo-D-Pro, as shown at page 137 of Vickery et al above, and the like.

At position 2, the His can be present or replaced with, for example, Halo-D-Phe, $NO_2$-D-Phe, or Dihalo-D-Phe, as shown in U.S. Pat. No. 4,444,759; Phe, D-Ala, and substituted D-Ala, substituted D-Phe and diphenyl Gly, as shown in U.S. Pat. No. 4,341,767 or the substituted D-Phe's shown in U.S. Pat. No. 4,431,635.

At position 3, the L-Trp group can be present or replaced, for example, with D-Trp, D-Phe, or substituted D-Ala or substituted D-Phe, as shown in U.S. Pat. No. 4,341,767, L-Phe, as shown in U.S. Pat. No. 4,431,635, D-NAL as shown by Rivier et al at page 14 of Vickery et al above.

At position 4, the Ser can be present or replaced, for example, with Gly, Ala, Met, Orn, Dap, Lys, Arg, or Pro, as set forth in the Table shown by Rivier, which also appears at page 14 of Vickery et al, above.

Similarly, at position 5, the Tyr group can be present or can be replaced, for example, by Cl-Phe, as shown by U.S. Pat. No. 4,444,759, or by Phe or any of the various o, m, or p halo Phe's shown by Rivier in the table at page 15 of Vickery et al.

The nature of position 6 has been very widely studied. The Gly group naturally present can remain, but also may be replaced. U.S. Pat. No. 4,410,514 suggests replacing Gly with a D isomer of any of 24 common and not so common $\alpha$ amino acids. U.S. Pat. No. 4,444,759 adds 4-$NH_2$-D-Phe as a possible 6 position substituent. U.S. Pat. No. 4,341,767 proposes a broad group of substituted Ala's having at their C3 position phenyls substituted with multiple alkyls, acyls, substituted cyclohexyls, or various heterocyclic acyl radicals. C. W. Beattie et al, *J Med Chem* (1975) 18.12: 1247, suggest a 2 methyl-Ala at position 6. U.S. Pat. No. 4,431,635 teaches that position 6 can be D-Trp, D-Phe, or a para-substituted D-Phe wherein the para-substituent is halo, nitro, amino, methyl, cyano, trifluoromethyl, hydroxy, or methoxy. Similarly, Vickery et al, above, at page 5, show t-Bu Ser, Nal, and Bzl-His, at page 17 show $Me_5$-D-Phe and pMe-D-Phe, at page 25 show Cha, Pfp, Mtf, Ptf, Tmp, Nal, and Dca, at page 26 show Bia, Dmb, Dcb, Boa, and Bta, and at page 31 show h-D-Arg(Et)$_2$ as 6 position materials.

At position 7, the Leu group can be present or replaced by N-Me-Leu, as shown by U.S. Pat. No. 4,444,759.

Position 8 is generally held as Arg, while the 9 and 10 positions are occupied by the Pro-KmGly-$NH_2$ or Pro-$H_2$KmGly-$NH_2$ group in accord with this invention.

The foregoing embodiments are presented as representative of the substitution patterns at positions 1 through 8 which the art has recognized can enhance or vary the pharmaceutical properties of the LHRH peptide. They are not presented as limitations on the substitutions possible for LHRH analogs incorporating the 9–10 ketomethylene or hydroxyethylene substitution of the invention.

Also without intention to limit the present invention one can identify certain 1–8 position LHRH substitution patterns which have been recognized by the art as providing enhanced LHRH agonist or antagonist response properties and which could have their oral activity enhanced by the use of the present invention. Such materials are given in Tables 3 and 4.

TABLE 3

| LHRH AGONISTS |
|---|
| [Pro$^9$—KmGly$^{10}$] LHRH, |
| [Pro$^9$—H$_2$KmGly$^{10}$] LHRH, |
| [R$^6$, Pro$^9$—KmGly$^{10}$] LHRH, and |
| [R$^6$, Pro$^9$—H$_2$KmGly$^{10}$] LHRH, |
| where R$^6$ is D-isomer of an $\alpha$-amino acid selected from Trp, Ala, Phe, Lys, Pro, Met, Leu, Glu, Asn, Arg, Tyr, Cys, His, Chg, Nva, Orn, Thr, Abu, Phg, Ile, Asp, Nle, Val, t-Bu—Ser, Nal, im-Bzl—His, and Cha, |
| [D-Trp$^6$, N—MeLeu$^7$, Pro$^9$—KmGly$^{10}$] LHRH, and |
| [D-Trp$^6$, N—MeLeu$^7$, Pro$^9$—H$_2$KmGly$^{10}$] LHRH. |

TABLE 4

| LHRH ANTAGONISTS |
|---|
| [Ac—D-Phe$^1$, D-pCl—Phe$^2$, D-Trp$_3$, D-Arg$^6$, Pro$^9$—KmGly$^{10}$] LHRH |
| [Ac—D-Phe$^1$, D-pCl—Phe$^2$, D-Trp$^3$, D-Arg$^6$, Pro$^9$—H$_2$KmGly$^{10}$] LHRH |
| [Ac—D-amino acid$^1$, D-Phe$^2$, D-Trp$^{3,6}$, Pro$^9$—KmGly$^{10}$] LHRH |
| [Ac—D-amino acid$^1$, D-Phe$^2$, D-Trp$^{3,6}$, Pro$^9$—H$_2$KmGly$^{10}$] LHRH |
| [Ac—D-Nal(2)$^1$, D-p-Cl—Phe$^2$, D-Trp$^3$, D-hArg(Et$_2$)$^6$, Pro$^9$—KmGly$^{10}$] LHRH |
| [Ac—D-Nal(2)$^1$, D-p-Cl—Phe$^2$, D-Trp$^3$, D-hArg(Et$_2$)$^6$, Pro$^9$—H$_2$KmGly$^{10}$] LHRH |

Synthesis of the Compounds

The polypeptides of the present invention may be synthesized by any techniques that are known to those skilled in the peptide art. An excellent summary of the many techniques so available may be found in J. M. Stewart and J. D. Young, *Solid Phase Peptide Synthesis*, W. H. Freeman Co., San Francisco, 1969, and J Meienhofer, *Hormonal Proteins and Peptides*, Vol. 2, p. 46, Academic Press (New York), 1973, for solid phase peptide synthesis, and E. Schroder and K. Lubke, *The Peptides*, Vol. 1, Academic Press (New York), 1965, for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

The preferred method for peptide synthesis for use herein involves synthesizing the peptide on a solid phase support.

In this process the Pro$^9$-KmGly$^{10}$, Pro$^9$-KamGly$^{10}$, or Pro$^9$-H$_2$KmGly$^{10}$ unit is first attached through its free COOH group to the support. In the case of the Pro$^9$-H$_2$KmGly$^{10}$ unit is attached as a suitably hydroxyl-group-protected derivative (e.g., a benzyl derivative). Then the desired 8, 7, 6 . . . etc. position amino acids are serially coupled to it. In this process, the α amino function of the amino acid being added is protected so that there is not repeat addition of any particular unit to a chain. The protecting group should be stable under the conditions of coupling but should be removable without any damage to the peptide chain or any racemization of bonds at any of the chiral centers of the chain.

Typical protecting groups include t-butyloxycarbonyl (Boc), 9-fluorenylmethoxycarbonyl (Fmoc) benzyloxycarbonyl (Cbz); p-toluenesulfonyl (Ts); 2,4-dinitrophenyl; benzyl (Bzl); biphenylisopropyloxycarboxycarbonyl, t-amyloxycarbonyl, isobornyloxycarbonyl, o-bromobenzyloxycarbonyl, cyclohexyl, isopropyl, acetyl, o-nitrophenylsulfonyl, and the like. Of these, Boc and Fmoc are preferred, with Fmoc being the most preferred protecting group.

To prepare the materials of the invention a suitably amine-protected 9–10 dipeptide group such as, for example, Fmoc-Pro-KamGly, benzylated Boc-Pro-H$_2$KmGly, or Boc-Pro-KmGly or the like is attached to a suitable solid support. Suitable supports useful for this synthesis are materials that are insoluble in the synthesis reagents. In addition, they should be inert to the reagents and conditions of the synthesis of the peptide chain.

Typical solid supports are generally classified as cross-linked polymeric supports. These can include divinylbenzene cross-linked styrene-based polymers, for example, divinylbenzene-hydroxymethylstyrene copolymers, divinylbenzene-chloromethylstyrene copolymers, and divinylbenzene-benzhydrylaminopolystyrene copolymers. The last of these materials is described by P. G. Pietta et al in *Chem Commun* (1970) 650, and offers the advantage of directly introducing the terminal amide function into the peptide chain, which function is retained by the chain when the chain is cleaved from the support.

The materials of this invention are generally prepared by coupling the protected 9–10 unit to the support, removing the protective group, and then serially adding and deprotecting the individual remaining amino acid residues. Typically, this is carried out in an automated or semiautomated peptide synthesizer such as the Peninsula Laboratories Peptider or the Beckman Model 990.

To illustrate this synthesis, two representative synthetic schemes for preparing —Km— materials, one using Boc protection and one using Fmoc protection, will now be described below. Then a synthesis route to —H$_2$Km— materials will be described.

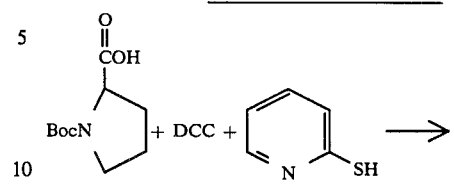

SYNTHESIS ROUTE 1
BOC—PROTECTION

-continued
SYNTHESIS ROUTE 1
BOC—PROTECTION

-continued
SYNTHESIS ROUTE 1
BOC—PROTECTION

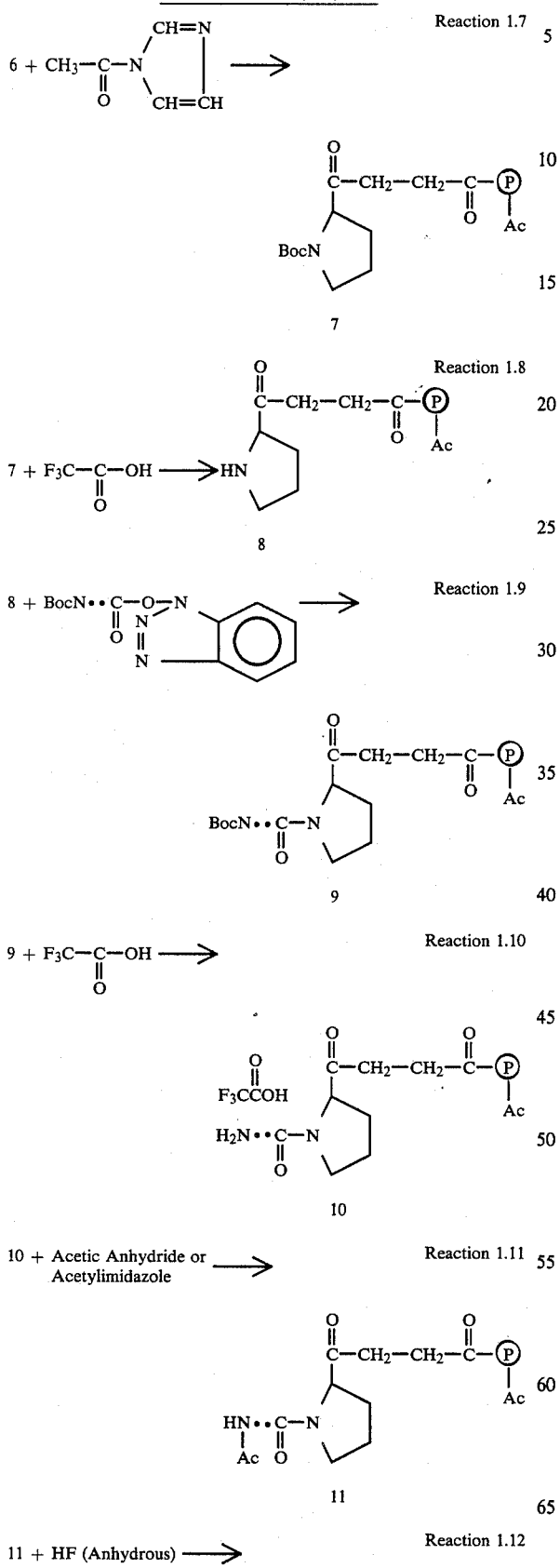
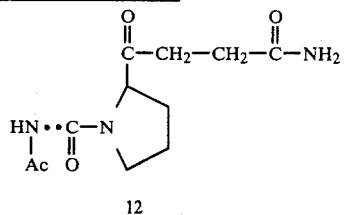

A reaction scheme for forming the Boc-protected 9–10 unit and incorporating it into an LHRH analog is depicted above as Synthesis Route 1. In this route, in reaction 1.1, Boc-protected proline is reacted with essentially equimolar amounts of dicyclohexylcarbodiimide (DCC) and 2-mercaptopyridine in a dry polar organic solvent such as ethyl acetate at a low to moderate temperature such as $-25°$ C. to $+35°$ C., preferably from $0°$ C. to $25°$ C., for from 5 to 30 hours.

In reaction 1.2 a Grignard reagent is prepared. This can be carried out as is known in the art. In a typical preparation, an essentially equimolar amount of 4-bromobutene is dripped into metallic magnesium that is stirred in a dry aprotic solvent such as diethyl ether or the like and stirred at, for example, room temperature for 1–4 hours. The Grignard reagent so formed is generally used as such a solution.

In reaction 1.3, the Grignard reagent produced in reaction 1.2 and reagent 1 are reacted to add the olefin group of the Grignard reagent to 1. This can be carried out by mixing the Grignard reagent with the pyridyl ester in a dry aprotic liquid such as THF or the like. At least one equivalent of Grignard reagent is used per equivalent of ester with 1:1 to 3:1 Grignard reagent to ester mole ratios being typical. The addition of the Grignard reagent is carried out at low temperature such $-25°$ C. to $+10°$ C. over a period of 0.25 to 2 hours, preferably $-10°$ C. to $0°$ C. over a period of about 0.5 hours.

In reaction 1.4 the olefinic double bond of the group added by the Grignard reagent is oxidized to a carboxyl group using an alkali metal metaperiodate such as $NaIO_4$ or $KIO_4$ and a catalyst such as ruthenium dioxide. An excess of periodate is used with olefin to periodate to ruthenium molar ratios of from 1:5:001 to 1:20:0.1 being typical. An aqueous solution of $RuO_2$ and periodate can be used along with a water-miscible organic liquid such as acetone, acetonitrile, or the like to aid dissolution of the organic reactant. Usually, this reaction is carried out at about $-10°$ C. to $+25°$ C. for 0.5 to 3 hours with $0°$ C. giving good reaction in about 1–1.5 hours.

In reaction 1.5, the acid product of reaction 1.4 is converted to the benzotriazole active ester to facilitate its coupling to the polymer. This reaction involves reacting acid product 4 with an essentially equimolar amount of 1-hydroxybenzotriazole in a dry mixed solvent such as methylene dichloride-DMF, 1:1 v/v, or the like in the presence of about an equimolar amount of a carbodiimide such as about 1.1 moles/mole of dicyclohexylcarbodiimide at $-10°$ C. to $+25°$ C., especially about $0°$ C. for from 0.1 to 1 hour, especially about 0.2 to 0.4 hour. The active ester 5 is generally used as a solution obtained by removing the solid precipitated disubstituted urea corresponding to the carbodiimide.

In reaction 1.6, the active ester 5 is coupled to the polymer. This can be carried out by adding the solution of 5 to the polymer resin along with about 1.5 equivalents of amine such as diisopropylethylamine to hold pH constant at about pH 6.5. This coupling can be carried out at about room temperature in 6 to 20 hours. If more complete substitution of the resin is desired, additional ester and additional time can be used. A Kaiser test or the like can be used at this point to determine whether or not the resin contains unreacted but potentially reactive sites. If such sites are present, the resin can be acetylated to block them from further reaction. This can be carried out as shown in reaction 1.7 by adding a substantial excess, for example, 3 to 20-fold, of 1-acetylimidazole and stirring at 0° C. to 30° C., especially about room temperature, for from 0.5 to 6 hours. Alternatively, acetylation could be carried out with acetic anhydride.

Following acetylation, the Boc protection is removed as shown in reaction 1.8. This can be carried out using nonaqueous strong acid such as hydrochloric acid, or trifluoroacetic acid in dioxane, methylene dichloride or an equivalent nonaqueous nonpolar organic solvent. Preferred deprotecting agents are 20–60% volume/volume trifluoroacetic acid in methylene dichloride optionally containing up to about 2% of indole or 2-mercaptoethanol scavenger. Deprotection can be accomplished in from 0.1 to 5 hours at 5° C. to 40° C., preferably being carried out in about 0.5 hours at room temperature. After deprotection, the resin can be washed free of acid, generally with a nonaqueous medium such as isopropanol in $CH_2Cl_2$ or the like.

The deprotected dipeptide-containing polymer product 8 is then coupled to the next amino acid desired in the peptide chain. As will be pointed out below, often, it is possible to achieve higher yields by adding two or more amino acids to the chain at one time to avoid problems with cyclization or the like. The amino acid or acids can be advantageously added as their benzotriazole active esters, which can be formed as described with reference to reaction 1.5. The coupling to the peptide chain is carried out at a pH of about 6.5–7, especially 6.5, which can be attained by adding an organic amine such as diisopropylethylamine in a suitable solvent such as $CH_2Cl_2$. About one equivalent of amine is generally required. The coupling of the 8,7,6, etc. position amino acids in reaction 1.9 generally takes somewhat less time than the time required to couple the 9–10 Pro-KmGly group to the resin with each coupling being carried out in from 0.5 to 4 hours at a temperature of 0° C. to 30° C., and especially about 2 hours at room temperature. An excess, often a 1.5 to 10-fold molar excess, of the Boc-protected amino acid is used. This excess can advantageously be added in several separate additions. Typically, the extent of coupling is monitored by the Kaiser test and coupling is continued until the test shows negative.

After coupling reaction 1.9 is complete, unreacted amine sites can be blocked (acetylated) such as with excess acetic anhydride at 0° C. to 20° C. in 1:1 v:v benzene:pyridine for 0.5 to 2 hours. Then, as shown in reaction 1.10, the Boc protection is removed, typically using the deprotecting conditions and reagents used in reaction 1.8. Reactions 1.9 and 1.10 are then repeated with appropriate protected amino acids until the desired LHRH analog as been constructed.

At that point the terminal amine is acetylated or otherwise protected as shown in reaction 1.11. This acetylation can be carried out using acetylimidazole and the conditions of reaction 1.7. Alternatively, it can be carried out using excess acetic anhydride in 1:3:3 volume ratio in pyridine and benzene for 0.5 to 2 hours at 0° C. to 20° C. The peptide is cleaved from the resin as shown in reaction 1.12 by contacting the resin with a strong acid. Anhydrous liquid HF (containing from 1 to 20% anisole or a similar carbonium ion scavenger and optionally 0.1 to 3% 2-mercaptoethanol) is the cleaving agent of choice. Reaction 1.12 can be completed in about an hour at 0° C. with times from 0.5 to 3 hours and temperature of −10° C. to +15° C. being generally useful.

While in general the amino acids are added one at a time, one may, if desired, add multiple amino acid residues, such as Boc-protected dipeptides, tripeptides, and the like. This can be advantageously employed to avoid inadvertent side reactions which may occur such as by cyclization of intermediates and the like. For example, when adding the "8" position Boc-protected amino acid, during the acidic Boc cleavage step, the free amine so formed can yield a 6-membered cyclic imine with the ketomethylene group. If a "7-8" dipeptide is coupled, the advantageously-formed 6-membered ring imine is avoided.

In an alternative and often preferred synthesis route, Fmoc protection is employed. This route is depicted in Synthetis Route 2.

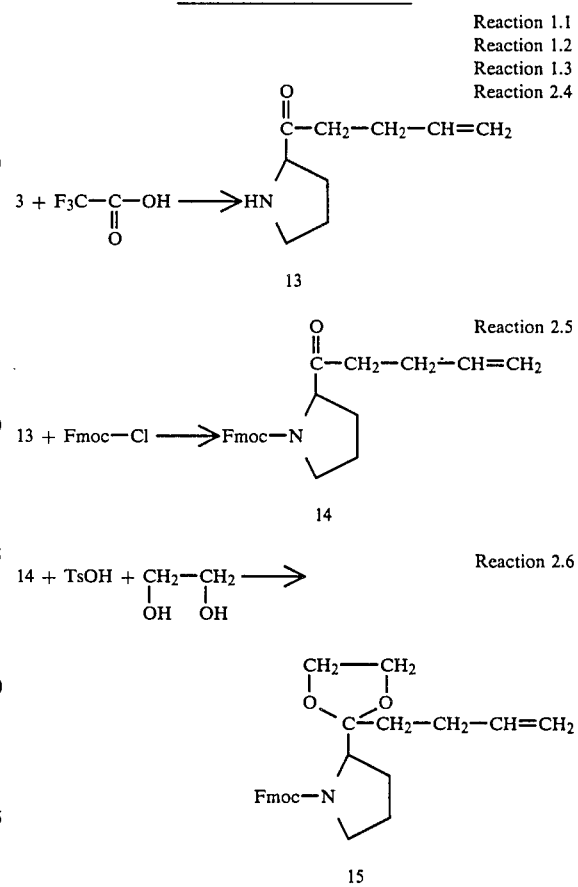

SYNTHESIS ROUTE 2
FMOC PROTECTION

-continued
SYNTHESIS ROUTE 2
FMOC PROTECTION

Reaction 2.7

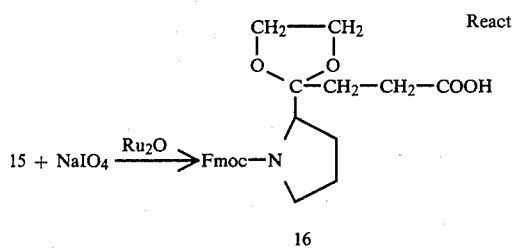

16

Reaction 2.8

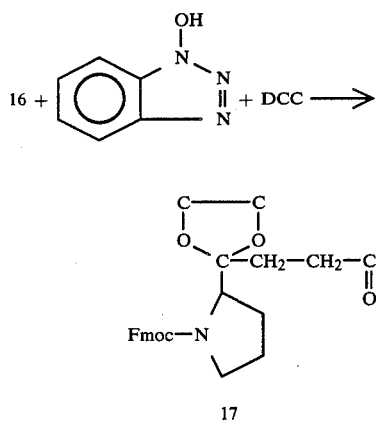

17

17 + Benzhydrylamino (P) polystyrene ⟶    Reaction 2.9

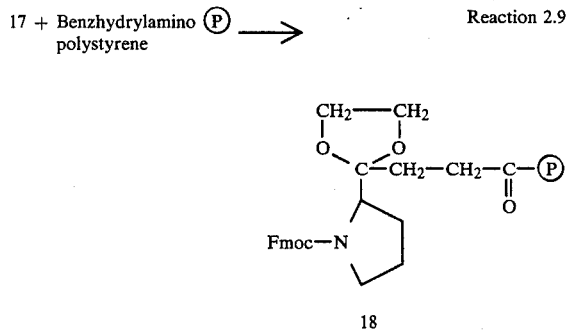

18

Reaction 1.7
Acetylation of residual sites on polymer to yield 18-Ac, 19

19 + 50% Piperidine in CH₂Cl₂ ⟶    Reaction 2.10

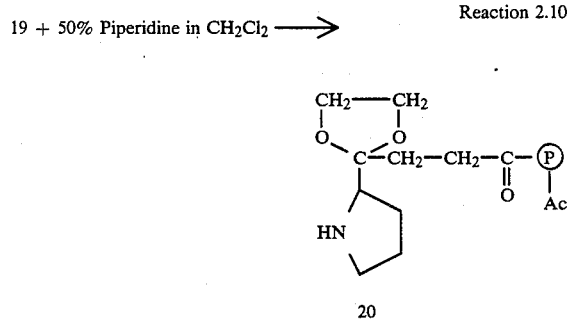

20

Reaction 2.11

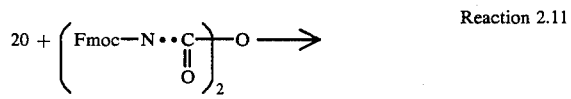

-continued
SYNTHESIS ROUTE 2
FMOC PROTECTION

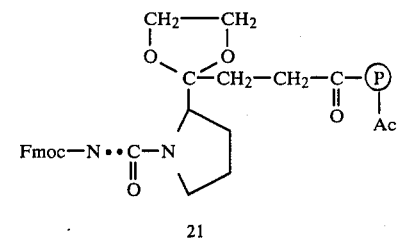

21

Repeat 1.7, 2.10 and 2.11 as required to give ultimate polymer bound peptide 22.

22 $\xrightarrow{\text{acetic anhydride pyridine benzene}}$ 22 - Ac    Reaction 2.12
23

23 + HF (Anhydrous) ⟶    Reaction 2.13

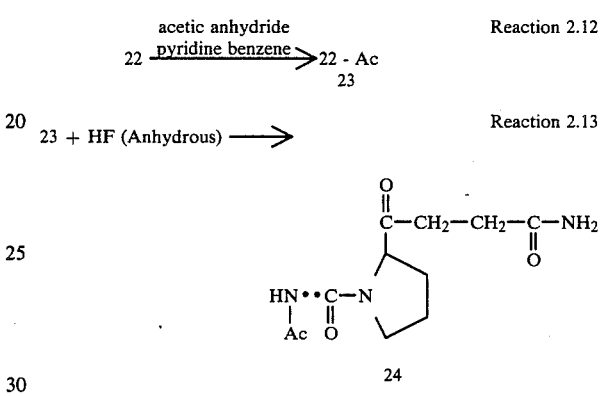

24

The route begins with reactions 1.1, 1.2, and 1.3 as shown in Route 1 above to give the Boc-protected, olefin-substituted proline 3. In reaction 2.4 the Boc protection is removed by contact with a molar excess of acid. Typically the acid is trifluoroacetic acid, although other equivalent acids such as hydrochloric acid can be used. This reaction is carried out in solution with a nonaqueous nonpolar organic solvent such as CH₂Cl₂ or dioxane or the like being suitable. This reaction is generally complete in about 0.1 to 0.5 hours at room temperature.

In reaction 2.5, the deprotected proline analog 13 is reprotected with Fmoc using conventional Fmoc protection methods. For example a solution of 13 can be slowly added to about 1 to 2 equivalents of 9-fluorenylmethylchloroformate and a substantial excess (i.e., 4 to 10 equivalents) of bicarbonate. This reaction can employ a mixed water-organic solvent such as water-THF. It can be carried out at low to moderate temperature such as −10° C. to +35° C. for times of from about 1 hour to about 12 hours. Four hours at 25° C. is a typical reaction time.

The Fmoc-protected proline analog 14 is converted to ketal 15 as shown in reaction 2.6. Material 14 is mixed with a large excess (such as a 100-fold molar excess) of ethylene glycol in a suitable dry nonpolar solvent such as toluene or the like in the presence of an acid. Paratoluene sulfonic acid or an equivalent acid can be used. This reaction is carried out at elevated temperatures such as 50° C. to 150° C. with the reflux temperature of the solvent being convenient. At 111° C. (toluene reflux temperature) the reaction requires from about 1 to 10 hours, usually being complete in about 7 hours.

In reaction 2.7, the olefinic bond of ketal product 15 is oxidized to an acid. The periodate/ruthenium dioxide reaction depicted as reaction 1.4 can be employed as can the conditions set forth for reaction 1.4. The reaction time may be extended, however, to from 1 to 5 hours, with 2 hours generally being adequate.

In reaction 2.8, acid 16 is converted to a hydroxybenzotriazole active ester for coupling to a solid support. This can be carried out by mixing equivalent molar amounts of acid 16 and 1-hydroxybenzotriazole in a suitable solvent such as $CH_2Cl_2/DMF$, 1:1 v/v, chilling, and adding about 1 to 1.5 equivalents of a carbodiimide coupling agent such as dicyclohexylcarbodiimide (DCC). After about 0.1 to 0.5 hours, the active ester 17 is formed.

In reaction 2.9, the active ester 17 is coupled to the polymer. This is carried out in the presence of added amine to hold the pH at about 6.5 to 7 and may be repeated one or more times to attain complete substitution. In general, the conditions, tests, and methods of reaction 1.6 can be used.

Unreacted reactive sites on the polymer (as indicated by the Kaiser test) can be acetylated using the method shown in reaction 1.7.

In reaction b 2.10, the peptide unit on the acetylated coupled polymer is deprotected using conventional Fmoc deprotection methods. In a typical deprotection method, an organic base such as piperidine is used to remove the Fmoc group. With a substantial molar excess of 50% piperidine in a nonpolar solvent such as methylene dichloride or dioxane, the Fmoc groups can be completely removed in about 0.5 hours at room temperature to yield deprotected product 20.

In reaction 2.11, the next amino acid residue is added to the peptide chain. This can be carried out by contacting the resin with a solution of the appropriate Fmoc-protected amino acid symmetrical anhydride. The anhydrides are prepared by the method of Wieland et al, *Justus Liebigs Ann Chem* (1973) 10:1595. An amine such as diisopropylethylamine can be advantageously added during coupling to hold pH at about 6.5 to 7. Coupling is carried out using an excess (1.5 to 5-fold) of the anhydride in a nonaqueous nonpolar solvent such as a methylene chloride-DMF mixed solvent. Coupling can be repeated as needed with the above-noted Kaiser test being useful for measuring the degree of coupling attained. This reaction can be carried out at moderate temperatures in the 5° C. to 35° C. range and is usually complete in from 0.5 to 1.5 hours, although with proline, L and D-arginine and tyrosine materials, somewhat longer times such as 1 to 2.5 hours may be required.

Following coupling of the amino acid residue, one can, if desired, acetylate unreacted sites such as by the method of reaction 1.7. Thereafter, deprotection and coupling reactions 2.10 and 2.11 are repeated with appropriate anhydrides until the LHRH analog structure is constructed. After the last coupling, the Fmoc group is removed as in reaction 2.10 to give the free amine 22, and the peptide is acetylated in reaction 2.12 such as by contact with 1:3:3 acetic anhydride:pyridine:benzene. This reaction is usually carried out at 0° C. to 20° C. for 0.5 to 2 hours and is usually complete in about an hour at room temperature to yield peptide 23.

In reaction 2.13, the acetylated peptide 23 is cleaved from the resin with anhydrous acid, in particular anhydrous HF containing from 2 to 20% anisole or a similar carbonium ion scavenger and 0.2 to 5% mercaptoethanol. This reaction is carried out at low to moderate temperature such as about −5° C. to +15° C. and takes from about 0.2 to about 2 hours, especially about 0.5 to 1 hour, at 0° to 5° C. This reaction removes the protecting groups and also converts the ketal function in the "Kam" group to a carbonyl group so as to yield the desired $Pro^9$-$KmGly^{10}$ LHRH analog.

After synthesis by either of these routes, the LHRH analog is purified. Typical purification procedures for the analogs, as well as intermediate work up and isolation procedures are shown in the examples, although alternative methods may, of course, be employed.

The $Pro^9$-$H_2KmGly^{10}$ materials are formed in an analogous manner. In general terms, the Grignard reagent addition product 3 of reaction 1.3 can be subjected to reduction as in reaction 3.1.

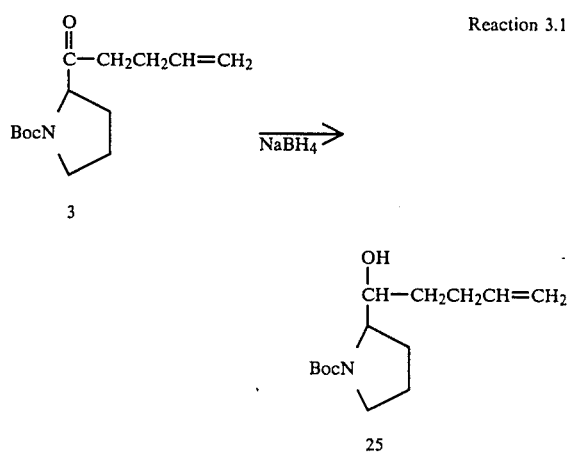

Reaction 3.1

This reaction is carried out at a temperature of from about 0° C. to 35° C., preferably about 25° C., for a time period of from 1 to 3 hours, preferably about 2 hours. This reaction is carried out in a polar solvent such as ethanol, THF, or methanol. The mole ratio of 3 to $NaBH_4$ is generally about 1:1 to about 1:1.5.

The hydroxy group obtained is protected, for example as a benzyl ether. The benzyl protecting group can be added by reaction with benzyl bromide as shown in Reaction 3.2.

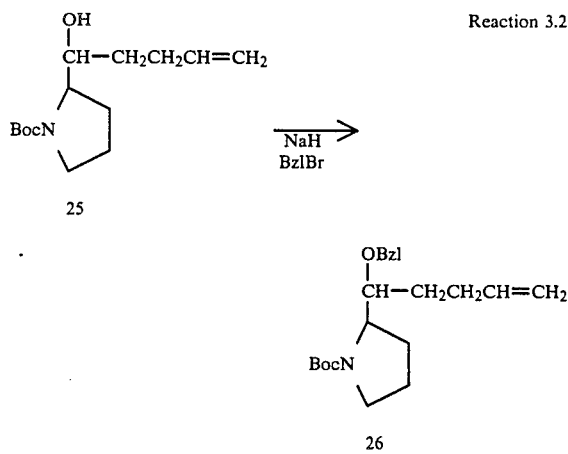

Reaction 3.2

This reaction is carried out at a temperature of from about 0° C. to about 35° C., preferably about 25° C. for a time period of from 2 to 64 hours, preferably about 16 hours. This reaction is carried out in a polar, aprotic solvent such as dimethylformamide or THF. The mole ratio of 25 to NaH and benzylbromide is generally from about 1:1:2 to about 1:2:10.

The Reaction 3.1 reduction yields an optically active center which gives rise to a mixture of R and S isomers. These can be identified by $^1$H-NMR examination of oxazolidinone derivatives of the two diastereoisomers as described by Futagawa et al, *Bull Chem Soc Japan* (1973) 46: 3308. These isomers can be separated by silica gel chromatography using ethyl acetate/hexane as eluent.

The Boc-protected, benzylated product 26 of Reaction 3.2 can be converted to the equivalent Fmoc-protected material at this point by reacting 26 in Reactions 2.4 and 2.5. The Boc-protected olefin 26 or its Fmoc equivalent can be converted to the corresponding acids by Reactions 1.4 or 2.7 respectively and employed in subsequent steps in reaction sequences 1 or 2. The Bzl-blocking group is left on the dipeptide during the oxidation of the double bond to the acid group in Reaction 1.4 or 2.7. It can be later removed in the Boc synthesis route by the HF cleavage step. In the Fmoc-protection route the benzyl blocking group can be removed at the time the peptide is cleaved from the resin in reaction 2.13.

When the above-described benzhydrylaminopolystyrene resin is used in the synthesis, the terminal acid function is cleaved from the solid resin together with an amine so as to directly yield the desired carboxy terminus amide function. When other resins are employed, this acid group may need to be converted to the amide after cleavage.

USE OF THE LHRH ANALOGS

The ketomethylene LHRH analogs of the this invention have the property of having enhanced pharmacologic activity when administered orally as compared to LHRH analogs which do not incorporate the ketomethylene substituents. The invention finds application with LHRH and its agonist analogs as well as LHRH antagonist analogs.

Although a primary thrust of the present invention involves enhanced oral activity of LHRH analogs, the compounds of the invention can be administered using any of the variety of routes known for pharmaceutical administration. Thus, the compounds can be administered orally, nasally, parenterally, i.e., intravenously, intramuscularly, and subcutaneously; by inhalation; vaginally, rectally, transdermally, and buccally.

The dose of LHRH analog administered is an effective dose which may depend upon the pharmacologic effect desired, the compound or compounds employed, and the mode of administration. In general terms, the materials of the present invention will often exhibit from 5 to 100 times the oral activity of similar materials not incorporating the ketomethylene functionality. This may not, however, be enough of an increase to completely offset the large activity advantage (i.e., often 1000-fold) often observed with parenteral administration or the moderate (i.e., 10 to 20-fold) activity advantages often observed with nasal administration. Accordingly, in general, the oral doses employed are often somewhat larger than the doses used parenterally. Typical dose ranges are from about 0.005 to about 20 mg/kg of body weight per day, with dose ranges in the range of from 0.01 to 15 mg/kg of body weight per day being preferred.

LHRH agonist materials can exhibit effects which give rise to clinical pharmaceutical utilities such as: male contraception, female contraception, treatment of precocious puberty, treatment of endometriosis, pregnancy interruption, treatment of breast tumors, and treatment of prostate tumors.

LHRH antagonist analogs can exhibit effects which give rise to clinical pharmaceutical utilities such as: female contraception by inhibition of ovulation, first trimester pregnancy interruption, male contraception by interruption of spermatogenesis, treatment of reproductive and nonreproductive tissue tumors and ectopic tumors, especially those secreting chorionic gonadotropin, therapy for endometriosis, and alleviation of the symptoms of menopause.

The LHRH analogs here provided can be formulated into pharmaceutical compositions by admixture with a pharmaceutically-acceptable nontoxic carrier. As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well known in the pharmaceutical art, for example as described in *Remington's Pharmaceutical Sciences*, Mack Publishing Company, Easton, Pa. 1970. Formulations for parenteral administration may contain as common excipients sterile water or saline, polyalkyene glycols such as polyethylene glycol, oils of vegetable origin, hydrogenated naphthalenes and the like. Formulations for vaginal or rectal administration, e.g., suppositories, may contain as excipients, for example, polyalkyleneglycols, vaseline, cocoa butter, and the like. Formulations for inhalation administration may be solid and contain as excipients, for example, lactose or may be aqueous or oily solutions for administration in the form of nasal drops. For buccal administration typical excipients include sugars, calcium stearate, magnesium stearate, pregelatinated starch, and the like.

The materials of this invention can be employed as the sole active agent in a pharmaceutical or can be used in combination with other active ingredients.

A number of tests are available for assaying the biological activity and potency of LHRH analogs of the invention.

An in vivo biological assay which can be used for LHRH antagonist analogs is described by Corbin and Beattie, *Endocrine Res Commun* (1975) 2: 1. The peptides are injected subcutaneously in corn oil or given orally at noon on the day of proestrus. The absence of, or a significant decrease in the number of, ova is the criterion for an antiovulatory effect. Results are expressed as number of animals ovulating and number of eggs recovered in ovulating rats.

An in vivo biological assay employing rats which can be used for LHRH agonist analogs is the 7-day post-coital assay described by Corbin et al at *Int J Gynaecol Obstet* (1979) 16: 359. Female rats receive daily administration of the peptides injected sc in corn oil or given orally on days 0–6 following coitus. On day 10 following coitus, the rats are autopsied and the absence of, or a significant decrease in the number of, fetuses is the criterion for an antifertility effect. Results are expressed as number of animals pregnant and number of normal and resorbing fetuses obtained.

Inhibition of LH and FSH release by the present compounds can be measured in vitro in dispersed anterior pituitary cell cultures by radioimmunoassay as shown by Vale et al, *Endocrinology* (1972) 91: 562.

This invention will be further described by the following preparations and examples. These are not to be construed as limitations on the scope of the invention but rather as merely being illustrative of the practice of the invention.

GENERAL

Materials

All chemicals and solvents used were of reagent grade. Solvents used for syntheses were purified by distillation prior to use and stored over Linde type 4A molecular sieves. DMF, pyridine, and diisopropylethylamine were distilled over ninhydrin under vacuum. Piperidine was distilled over KOH. Boc-protected and some Fmoc-protected amino acids were purchased from Chemical Dynamic and Peninsula Laboratories. Fmoc-D-Phe, Fmoc-D-p-Cl-Phe, Fmoc-D-Trp, Fmoc-L-Arg-(Ts), Fmoc-D-Arg(Ts), and Fmoc-Tyr (Br-Z) were prepared using the general procedure described by Chang et al in *Int J Pept Protein Res* (1980) 15: 59 for making Fmoc-amino acids. 9-fluorenylmethyl chloroformate was obtained from Aldrich Chemical Co. D-p-Cl-Phe was obtained by the enzymatic resolution of a DL mixture by the procedure described by Tong et al in *Can J Biochem* (1971) 49: 877. Purity of Fmoc-amino acids was accessed by TLC. Benzhydrylamine resin hydrochloride was purchased from Peninsula Laboratories.

Methods

Melting points were determined on a Thomas-Hoover Uni-melt and are uncorrected. Optical rotations were measured on a Perkin-Elmer 141 automatic polarimeter. Mass spectra were taken with either an LKB 9000 GC-MS spectrometer or a Reibermag Model R-10-10-C using desorption chemical ionization. $^1$H NMR spectra were taken with a Varian EM 390 spectrometer. $^{13}$C NMR spectra were taken on a JEOL FX 90Q spectrometer. Evaporations were performed at 40° C. under house vacuum (35 mm Hg) on a Büchi rotovapor unless otherwise stated. Elemental analyses were conducted by a commercial analytical laboratory. Thin-layer chromatography was performed on silica gel GF plates (Analtech) using solvent systems as described below. The plates were visualized by UV absorption, followed by ninhydrin spray or chlorination ($Cl_2$) and 1% KI/starch spray. Analytical HPLC was performed on Waters Model 6000A, equipped with a 20 μl loop injector and a Vydac TP21854 reverse phase column. The eluent was filtered and vacuum degassed. Acetonitrile, HPLC Grade (Burdick and Jackson) and MilliQ distilled water was used as HPLC eluents. TFA for HPLC was distilled. The column effluent was monitored at 220 nm with a Schoeffel SF770 spectroflow detector. Samples for amino acid analysis were sent to the University of California, Davis, Health Science Research Laboratories.

Unless otherwise noted, metric units are employed.

PREPARATION OF REPRESENTATIVE INTERMEDIATES

Preparations 1, 2 and 3

1-t-butoxycarbonyl-2-(S)-(pent-4-eno-1-yl)pyrrolidine (Compound 3) and Compounds 1 and 2 by reactions 1.1, 1.2, and 1.3

To a stirred solution of N-t-butoxycarbonyl-L-proline (20.1 g, 93.5 mmol) and 2-mercaptopyridine (10.4 g, 93.5 mmol) in dry, degassed EtOAc (1 L) at 0° C. under argon, was added dicyclohexylcarbodiimide (DCC) (19.3 g, 93.5 mmol). The mixture was stirred 45 min at 0° C. and then 16 hr at ambient temperature. The mixture was cooled in an ice bath, filtered, and the filtrate washed successively with saturated NaCl solution (500 mL), ice cold 0.5N NaOH (500 mL) and saturated NaCl solution (500 mL). the organic phase was dried (Drierite) and evaporated to a yellow oil which was dissolved in $Et_2O$/hexanes and evaporated to give compound 1, a light yellow crystalline solid: yield 30.2 g. To a solution of this mercaptopyridyl ester 1 in dry THF (400 mL) at −5° C. under argon was added 60 mL of a solution of the Grignard reagent 2 prepared as shown in reaction 1.2 by the dropwise addition of 4-bromo-1-butene (31.5 g, 233 mmol) over 1.5 hr to a mixture of Mg turnings (5.68 g, 234 mmol) in dry $Et_2O$ (90 mL) under argon. This caused reaction 1.3 to occur. TLC (30% EtOAc/hexanes) at this point indicated the absence of mercaptopyridyl ester 1. The reaction was poured into saturated $NH_4Cl$ solution (500 mL) and extracted with EtOAc (500 mL). The organic layer was collected and washed successively with 0.5N NaOH (2×500 mL) and saturated NaCl solution (500 mL). The EtOAc solution was dried (Drierite) and evaporated to a yellow oil: yield 26.4 g. This oil was eluted through a silica gel column (750 g, 90–200 mesh) with 1–20% EtOAc-petroleum ether (bp 35°–60° C.). The fractions corresponding to product Rf 0.50 (EtOAc-petroleum ether (bp 35°–60° C.), 1:4) were combined and evaporated to a colorless oil 3: yield 15.8 g (66.7%); $[\alpha]_D^{24}$ −60.1 (c 4.06, $CHCl_3$); $^1$H NMR ($CDCl_3$) δ1.41, 1.47 (2 s, 9, $C(CH_3)_3$), 2.1 (m, 8), 3.50 (m, 2, $NCH_2$), 4.27 (m, 1, NCH), 4.96 (d, 1, J=10 Hz, CH=$CH_2$), 5.02 (d, 1, J=17 Hz, CH=$CH_2$), 5.7 (ddt, 1, J=10, 17, 3 Hz); MS, m/e 252 (M—H); IR 1720, 1700 s (CO, NC(O)O). Anal. ($C_{14}H_{23}NO_3$) C, H, N.

Preparation 4

1-t-butoxycarbonyl-2(S)-(3-carboxypropano-1-yl)pyrrolidine (4) (Boc-Pro-KmGly) by reaction 1.4

To a solution of 3 (9.24 g, 36.5 mmol) in acetone (500 mL) at 0° C. was added a solution of ruthenium dioxide (51.2%, 242 mg, 0.932 mmol) and sodium metaperiodate (39.0 g, 182 mmol) in $H_2O$ (260 mL) at 0° C. over the course of 30 sec. The dense brown mixture was stirred 45 min at 0° C. and then filtered through Celite. 2-propanol (5 mL) was added to the filtrate and this mixture stirred for 10 min at ambient temperature. The mixture was saturated with NaCl and extracted with $CHCl_3$ (2×1 L). The $CHCl_3$ extracts were combined, washed with saturated NaCl solution (1 L), filtered through Celite, dried ($Na_2SO_4$) and evaporated to a dark oil: yield 10.8 g. This oil was dissolved in $CHCl_3$ (200 mL) and stirred with a solution of $NaHCO_3$ (10 g) in $H_2O$ (400 mL). The mixture was poured into a separatory funnel and the aqueous phase collected. This was cooled to 0° C., CHCl$_3$ (400 mL) was added, and the mixture acidified with cold, dilute HCl to pH 3. The CHCl$_3$ extract was washed with saturated NaCl solution (400 mL), dried (Na$_2$SO$_4$) and evaporated to a pale yellow gum which was crystallized from EtOAc-hexanes to white solid 4: yield 6.20 g (62.7%; mp 89°–91° C.; TLC R$_f$ 0.55 (CHCl$_3$-MeOH-HOAc, 9:1:0.05); [α]$_D^{20}$ −65.0 (c 4.28, CHCl$_3$); $^1$H NMR (CDCl$_3$) δ1.40, 1.46 (2 s 9, C(CH$_3$)$_3$), 1.88 (m, 4, CHCH$_2$CH$_2$), 2.68 (m, 4, C(O)CH$_2$CH$_2$C(O)OH), 3.50 (m, 2, NCH$_2$), 4.30 (m, 1, NCH), 9.55 (s, 1, COOH); MS m/e 270 (M—H); $^{13}$C NMR (CDCl$_3$) δ (peak height, mm) 23.67 (53), 24.26 (36), 27.38 (117), 28.29 (215), 28.81 (35), 29.85 (53), 33.10 (45), 33.62 (32), 46.82 (66), 64.71 (37), 65.16 (48), 80.44 (13), 154.5 (4), 155.5 (3), 177.27 (24), 177.53 (17), 208.23 (35, ketone). Anal. (C$_{13}$H$_{21}$NO$_5$) C, H, N.

Preparation 5

Hydroxybenzotriazole active ester of Boc-Pro-KmGly (5) by reaction 1.5

Dipeptide 4 and 1-hydroxybenzotriazole (3 equivalents each) were dissolved in CH$_2$Cl$_2$:DMF (1:1, v/v) and the solution cooled in an ice water bath. DCC (3 equivalents+10%) was added and the mixture was stirred for 15 minutes. Precipitated dicyclohexyl urea was filtered off and filtrate containing active ester 5 was retained for use in the Examples.

Preparation 6

Synthesis of Boc-protected Leu-Arg dipeptide unit

This dipeptide unit was synthesized via N-hydroxysuccinimidyl ester by the method of Anderson et al, *J Am Chem Soc* (1964) 86: 1839.

(a) Boc-Leu-OSu: 4.98 g (20 mmol) of Boc-Leu.H$_2$O and 2.52 g (22 mmol) of N-hydroxysuccinimide were dissolved in 40 mL of dry THF and the solution cooled in ice water bath. 4.54 g (22 mmol) of DCC was added with stirring. The reaction mixture was stirred in ice water bath for 2 hr and then at room temperature overnight. TLC showed the reaction was complete. Precipitated dicyclohexyl urea was filtered off. Filtrate was dissolved in ether and left in a refrigerator for 1 hr. More dicyclohexyl urea precipitated and was filtered off. The residue was coevaporated twice with hexane. Boc-Leu-OSu as a solid powder was obtained and washed with hexane and dried. Yield 6.34 g (96.7%), m.p. 91°–92° C.; R$_f$ 0.52 (CHCl$_3$:MeOH:HAc 9:1:0.1 v/v); 0.83 (n-BuOH:HAc:H$_2$O 4:1:1).

(b) TFA.Arg (Tos): 8.56 g (20 mmol) of Boc-Arg (Tos) was dissolved in 20 mL of TFA and the solution was allowed to stand at room temperature for 1 hr. TLC showed deprotection was complete. Acid was evaporated completely. The residue was triturated with anhydrous ether. The solid obtained was filtered, washed thoroughly with ether, and dried under high vacuum: yield 8.9 g (quantitative); m.p. 48°–50° C.; R$_f$ 0.39 (n-BuOH:HAc:H$_2$O 4:1:1 v/v).

(c) Boc-Leu-Arg (Tos): 8.90 g (20 mmol) of TFA-.Arg (Tos) was dissolved in 30 mL of water and 3.36 g (40 mmol) of NaHCO$_3$ was added with vigorous stirring. pH of the solution was ~7. 5.90 g (18 mmol) of Boc-Leu-OSu was dissolved in 20 mL of dioxane and added dropwise. The reaction mixture was stirred at room temperature overnight. TLC showed the disappearance of Boc-Leu-OSu. Dioxane was evaporated and the aqueous solution was diluted with water and cooled in ice water. It was acidified to pH 3 with ice cold 1N HCl. A white solid was extracted into EtOAc. Organic phase was washed with 0.1N HCl and thrice with water. It was dried over anhydrous sodium sulfate and evaporated. Residue was triturated with ether-hexane (1:9 v/v). A white solid powder product was obtained by filtration, washed with hexane, and dried: yield of Boc-Leu-Arg (Tos) 8.74 g (89.7% m.p. 89°–91° C.; R$_f$ 0.2 (CHCl$_3$:MeOH:HAc, 9:1;0.1 v/v); 0.80 (n-BuOH:HAc:H$_2$O, 4:1:1 v/v).

Preparation 7

1-(9-fluorenylmethoxycarbonyl)-2(S)-(pent-4-enol-1-yl)pyrrolidine (14) by reactions 2.4 and 2.5

In accordance with reaction 2.5, to a solution of 9-fluorenylmethylchloroformate (15.4 g, 59.7 mmol) and sodium bicarbonate (28.7 g, 271 mmol) in 2:1 H$_2$O/THF (600 mL) at 0° C. was added dropwise a solution in 1:1 H$_2$O/THF of the product 13 obtained by treatment of 3 (13.7 g, 54.2 mmol) with 3:1 CH$_2$Cl$_2$/TFA (200 mL) in Reaction 2.4 for 15 min at 25° C. followed by evaporation in vacuo. The mixture was stirred 4 hr at 25° C. and H$_2$O (500 mL) was added and the mixture was cooled to 0° C. The solid 14 was collected and washed with H$_2$O followed by hexane. Upon drying, white solid 14 was obtained: yield 15.7 g (77.3%); mp 135°–136° C.; TLC R$_f$ 0.33 (25% EtOAc/hexanes); [α]$_D^{20}$ −33 (c 0.55, CHCl$_3$); $^1$H NMR (CDCl$_3$) δ2.1 (m, 8, 3.50 (m, 2, NCH$_2$), 4.3 (m, 4), 4.9 (m, 2, CH=CH$_2$), 5.7 (m, 1, CH=CH$_2$), 7.4 (m, 8, aromatic); MS m/e 375 (M+); IR 1670, 1640 s (CO, NC(O)O). Anal. (C$_{24}$H$_{25}$NO$_3$) C, H, N.

Preparation 8

2-(but-3-enyl)-2-(1-(9-fluorenylmethoxycarbonyl)pyrrolidone-(S)-yl)-1,3-dioxolane (15) by reaction 2.6

A mixture of 14 (410 mg, 1.09 mmol), dry toluene (15 mL), ethylene glycol (5 mL) and p-toluenesulfonic acid was stirred and slowly distilled over 7 hr with periodic replacement of toluene. The mixture was allowed to cool, and the ethylene glycol was separated from the toluene in a separatory funnel. The toluene layer was diluted with more toluene to a volume of 50 mL and washed successively with saturated NaHCO$_3$ solution (50 mL) and saturated NaCl solution (50 mL). The organic phase was dried (Drierite) and evaporated to a colorless film which was purified by preparative silica gel TLC (hexanes-EtOAc-iPrOH, 75:25:2) to give 15: yield 335 mg (73.3%); TLC R$_f$ 0.46 (hexanes-EtOAc, 3:1); [α]$_D^{20}$ −35.0 (c 5.7, CHCl$_3$): $^1$H NMR (CDCl$_3$) δ1.8 (m, 8), 3.50 (m, 2), 3.85 (s, 4, ketal CH$_2$s), 4.3 (m, 4), 4.9 (m, 2, CH=CH$_2$), 5.7 (m, 1, CH=CH$_2$), 7.4 (m, 8, aromatic); MS m/e 419 (M+). Anal. (C$_{26}$H$_{29}$NO$_4$) C, H, N.

Preparation 9

2-(2-carboxyethyl)-2-(1-(9-fluorenylmethoxycarbonyl)-pyrrolidine-(S)-yl-1,3-dioxolane (Fmoc Pro-KamGly) (16) by reaction 2.7

To a solution of 15 (6.78 g, 16.2 mmol) in acetone (300 mL) at 0° C. was added an ice cold solution of ruthenium dioxide (51.2%, 110 mg, 423 μmol) and sodium metaperiodate (17.3 g, 80.8 mmol) in H$_2$O) 150 mL). After 2 hr at 0° C., the mixture was filtered through Celite, poured into H$_2$O (250 mL) and extracted with CHCl$_3$ (2×500 mL) which was washed with H$_2$O (250 mL) and saturated NaCl solution (250 mL). The combined organic extracts were dried (Na$_2$SO$_4$) and evaporated to an amber gum. This gum was dissolved in Et$_2$O (100 mL) and partitioned with H$_2$O (250 mL) containing Na$_2$CO$_3$ (2 g). The aqueous phase was collected, acidified to pH 3 with dilute HCl and extracted with Et$_2$O (250 mL). The organic phase was washed with saturated NaCl solution, dried (Na$_2$SO$_4$) and evaporated to a colorless foam. This foam was purified by preparative high performance reversed phase liquid chromatography (MeOH-0.05% TFA, 3:1). Fractions containing product were combined, reduced to ~50% volume, and chilled. The solution was decanted from the gum and the gum was washed with H$_2$O (100 mL). The gum was dissolved in Et$_2$O (100 mL), washed with H$_2$O (2×100 mL) and saturated NaCl solution (100 mL), dried (Na$_2$SO$_4$), and evaporated to a white foam 16: yield 3.95 g (55.9%); $[\alpha]_D^{20}$ −34.5 (c 1.005, CHCl$_3$); $^1$H NMR $\delta$1.8 (m, 6), 2.4 (m, 2), 3.50 (m, 2), 3.85 (s, 4, ketal CH$_2$s), 4.3 (m, 2), 4.5 (m, 2), 7.4 (m, 8, aromatic), 8.7 (bs, 1, COOH); $^{13}$C NMR (CDCl$_3$) $\delta$ (peak height, mm (23.93 (20), 26.60 (23), 28.22 (44), 30.17 (34), 47.21 (53), 47.41 (60), 61.52 (62), 65.42 (54), 65.88 (51), 67.11 (48), 111.98 (15), 119.85 (140), 124.99 (125), 126.94 (130), 127.59 (119), 141.3 (29), 144.04 (26), 156.20 (22), 178.84 (33, COOH); MS m/e 438 (M+H). Anal. C$_{25}$H$_{27}$NO$_6$ (C, H, N).

Preparation 10

Active Ester of Fmoc Pro-KamGly

Fmoc-Pro-KamGly, prepared in preparation 9, and 1-hydroxybenzotriazole (3 equivalents of each) were dissolved in 1:1 v/v methylene chloride:DMF and the solution was cooled in an ice bath. Dicyclohexylcarbodiimide (3 equivalents+10%) was added and the mixture was stirred for 15 minutes. Precipitated dicyclohexyl urea was filtered off and the filtrate containing the desired active ester was retained.

Preparation 11

1-t-Butoxycarbonyl-2-(S)-(1-((S,R)-hydroxy)-pent-4-en-1-yl)pyrrolidine (25) by reaction 3.1

Sodium borohydride (288 mg, 7.60 mmol) was added to a solution of 3 (7.00 g, 27.6 mmol) in EtOH (125 mL) and the mixture stirred under an argon atmosphere for 16 hr. The mixture was poured onto saturated NH$_4$Cl solution (125 mL) and extracted with CHCl$_3$ (2×125 mL) which was washed with saturated NaCl solution, dried (Na$_2$SO$_4$) and evaporated to a yellow liquid: yield 6.76 g. The crude material which was a mixture of the S and R diastereoisomers was purified and separated into its components by silica gel flash chromatography (200 g, 230-400 mesh) eluting with 20% EtOAc-petroleum ether (bp 35°-60° C.) to give the (S) alcohol 25S: yield 3.54 g (50.1%), mixed fractions 716 mg (10.1%) and (R) alcohol 25R 1.77 g (25.1%). 25S TLC R$_f$ 0.51 (EtOAc-petroleum ether (bp 35°-60° C.), 1:3); $[\alpha]_D^{23}$ −64.2 (C 1.72, CHCl$_3$); $^1$H NMR (CDCl$_3$) $\delta$1.46 (s, 9, (CH$_3$)$_3$), 2 (m, 9), 3.5 (bm, 3), 3.8 (bm, 1), 5.0 (m, 2), 5.8 (m, 1); MS, m/e 256 (m+H); IR 3600-3200 S (OH). Anal (C$_{14}$H$_{25}$NO$_3$) C, H, N. 25R: TLC R$_f$ 0.39 (EtOAc-petroleum ether (bp 35°-60° C.), 1:3); $[\alpha]_D^{23}$ −42.0 (C 0.81, CHCl$_3$); $^1$H NMR (CDCl$_3$) $\delta$1.46 (5, 9, (CH$_3$)$_3$); 1.8 (m, 5), 2.2 (m, 3), 3.5 (bm, 5), 5.0 (m, 2), 5.8 (m, 1); MS, m/e 256 (m+H); IR 3600-3200 S (OH). Anal (C$_{14}$H$_{25}$NO$_3$) C, H, N.

Determination of the Stereochemistry of the Hydroxyl of Alcohols 25S and 25R

Compound 25S was treated with a solution of TFA-CH$_2$Cl$_2$ (1:1) for 30 m and evaporated in vacuo. The resulting oil was dissolved in CH$_2$Cl$_2$ and washed with dilute NaOH solution, the organic phase was collected, dried (Na$_2$SO$_4$) and evaporated to give the free amine which was reacted with carbonyldiimidazole (1 eq.) in CH$_2$Cl$_2$ for 16 hr. The solution was poured into H$_2$O and the organic phase collected, washed with saturated NaCl solution, dried (Na$_2$SO$_4$) and evaporated to give the crude oxazoidinone which was purified by preparative TLC on silica gel eluting with EtOAc-hexanes (1:1). Oxazolidinone off 25S: TLC R$_f$0.39 (EtOAc-hexanes, 1:1); $^1$H NMR (90 MHz, CDCl$_3$) $\delta$2 (m, 8), 3.24 (m, 1), 3.68 (m, 2), 4.38 (m, 1), 5.10 (m, 2), 5.89 (m, 1); $^1$H 400 MHz NMR for the oxazolidinone OC$\underline{H}$ $\delta$4.386 (ddd, 1, J=3.90, 5.37, 7.81 Hz); for the oxazolidinone NC$\underline{H}$ $\delta$3.631 (ddd, 1, J=3.90, 5.86, 9.28 Hz) J NC$\underline{H}$, OC$\underline{H}$=3.90 Hz which implies trans, or (S) configuration for the hydroxyl of 25S; MS m/e 181 (m).

The above procedure was repeated with 25R to give the following results. Oxazolidinone of 25R: TLC R$_f$ 0.30 (EtOAc-hexanes, 1:1); $^1$H NMR (90 MHz, CDCl$_3$) $\delta$1.8 (m, 8), 3.26 (m, 1), 3.75 (m, 2), 4.74 (m, 1), 5.10 (m, 2), 5.89 (m, 1); $^1$H 400 MHz, NMR for the oxazolidinone OC$\underline{H}$ $\delta$4.738 (ddd, J=4.89, 7.33, 8.79 Hz), for the oxazolidinone NC$\underline{H}$ $\delta$3.872 (ddd, J=5.37, 7.33, 11.23 Hz); J NC$\underline{H}$, OC$\underline{H}$=7.33 Hz which implies cis, or (R) configuration for the hydroxyl of 25R, MS m/e 181 (m).

Preparation 12

Protecting Materials 25S and 25R by reaction 3.2 to give 2(S)-(1-((S or R)-Benzoxy)pent-4-en-1-yl)-1-(t-butoxycarbonyl)-pyrrolidine 26(S) or 26(R)

The (S) alcohol 25(S) (2.09 g, 8.18 mmol) was dissolved in DMF (20 mL) and benzyl bromide (10 mL) under argon and cooled to 0° C. To this solution was added sodium hydride (508 mg, 58% oil dispersion, 12.2 mmol) and the mixture was allowed to come to ambient temperature over 16 hours with stirring. The mixture was poured into ice-cold saturated NH$_4$Cl solution (75 mL) and extracted with Et$_2$O (3×75 mL) which was washed with H$_2$O (2×75 mL) and finally saturated NaCl solution (75 mL). The combined ether extracts were dried (Na$_2$SO$_4$) and evaporated. The crude product was purified by flash chromatography on silica gel (160 g, 230-400 mesh) eluting with 10% EtOAc-petroleum ether (bp 35°-60° C.) to give the product 26(S) as a colorless oil: yield 1.94 g (68.5%); TLC R$_f$ 0.43 (EtOAc-petroleum ether (bp 35°-60° C.), 1:9); $[\alpha]_D^{23}$−31.4 (C 0.36, CHCl$_3$); $^1$H NMR (CDCl$_3$) $\delta$1.47 (s, 9, (CH$_3$)$_3$), 2 (m, 8), 3.3 (bm, 2), 3.8 (bm, 1), 4.1 (bm, 1), 4.48 (d, 1, J=10.5 Hz, one proton of OC$\underline{H}_2$Ph), 4.67 (d, 1, J=10.5 Hz, one proton of OC$\underline{H}_2$Ph), 5.0 (m, 2), 5.8 (m, 1), 7.30 (s, 5, Ph); MS, m/e 345 (m). Anal (C$_{21}$H$_{31}$NO$_3$) C, H, N.

The (R) alcohol 25R (1.17 g, 4.58 mmol) was similarly converted to the (R) benzyl ether 26R: yield 1.10 g (69.6%); TLC R$_f$ 0.48 (EtOAc-petroleum ether (bp 35°-60° C.), 1:9); $[\alpha]_D^{23}$−62.0 (C 2.43, CHCl$_3$); $^1$H NMR (CDCl$_3$) $\delta$1.47 (s, 9, (CH$_3$)$_3$), 2 (m, 8), 3.3 (bm, 2), 3.9 (bm, 2), 4.50 (s, 2, OC$\underline{H}_2$Ph), 5.0 (m, 2), 5.8 (m, 1), 7.27 (s, 5, Ph), MS, m/e 345 (m). Anal ($C_{21}H_{31}NO_3$) C, H, N.

Preparation 13

Oxidation of ethers 26R and 26S to 2(S)-(1-((S or R)Benzoxy)-3-carboxyprop-1-yl)-1-(t-butoxycarbonyl)-pyrrolidine (27R and 27S) (Boc-Pro-BzlH$_2$KmGly) via reaction 1.4

To a stirred solution of the (S) benzyl ether 26(S) (1.81 g, 5.23 mmol) in acetone (90 mL) at 0° C. was added an ice cold solution of ruthenium dioxide (51.2%, 35 mg, 135 μmol) and sodium metaperiodate (5.59 g, 26.1 mmol) in H$_2$O (45 mL) over the period of one minute. After 1 hour at 0° C., the ice bath was removed and the mixture allowed to reach ambient temperature over 3 hours. The mixture was filtered through Celite, poured into H$_2$O (250 mL) and extracted with CHCl$_3$ (3×300 mL) which was washed with H$_2$O (300 mL) and saturated NaCl solution (300 mL). The combined organic extracts were dried (Na$_2$SO$_4$) and evaporated to a yellow gum. This gum was dissolved in Et$_2$O (100 mL) and extracted with 0.05M NaHCO$_3$ solution (3×100 mL). The aqueous extracts were combined, cooled to 0° C., acidified with cold, dilute HCl solution to pH 3 and extracted with CHCl$_3$ (2×100 mL). The chloroform extracts were combined, washed with saturated NaCl solution (100 mL), dried (Na$_2$SO$_4$) and evaporated to a colorless gum 27(S): yield 1.19 g (63.2%); $[\alpha]_D^{23}$ −53.4 (C 1.72, CHCl$_3$); $^1$H NMR (CDCl$_3$) δ1.47 (s, 9, (CH$_3$)$_3$), 1.8 (bm, 6), 2.4 (bm, 2), 3.3 (bm, 2), 3.9 (bm, 1), 4.2 (bm, 1), 4.45 (d, 1, J=10.5 Hz, one proton of OCH$_2$Ph), 4.64 (d, 1, J=10.5 Hz, one proton of OCH$_2$Ph), 7.28 (s, 5, Ph), 9.1 (bs, 1, COOH); MS, m/e 363 (m). Anal ($C_{20}H_{29}NO_5$), C, H, N.

The (R) benzyl ether olefin, 26R, (2.18 g, 6.30 mmol) was similarly converted to the (R) benzyl ether acid 27R: yield 2.07 g (90.6%); $[\alpha]_D^{23}$ −46.7 (C 2.83, CHCl$_3$); $^1$NMR (CDCl$_3$) δ1.47 (s, 9, (CH$_3$)$_3$), 1.8 (bm, 6), 2.4 (bt, 2, J=7 Hz, CH$_2$COOH), 3.3 (bm, 2), 3.8 (bm, 1), 4.0 (bm, 1), 4.50 (s, 2, OCH$_2$Ph), 7.27 (s, 5, Ph), 10.1 (bs, 1, COOH); MS, m/e 345 (m). Anal ($C_{20}H_{29}NO_5$) C, H, N.

EXAMPLE 1

Synthesis of Ac[D-Phe[1], D-p-Cl-Phe[2], D-Trp[3], D-Arg[6], Pro-KmGly[9,10]] LHRH using Boc protection and reactions 1.6, 1.7, 1.8, 1.9, 1.10, 1.11 and 1.12

The peptide was synthesized on a Beckman 990 automated peptide synthesizer. Boc-Pro-KmGly was coupled to the benzhydrylaminopolystyrene-2% divinylbenzene resin described by Pietta et al, *Chem Commun* (1970) 650, as its preformed benzotriazole active ester 6 (as prepared in preparation 5). After adding benzotriazole ester, 1.2 equivalents of diisopropylethylamine in CH$_2$Cl$_2$ (0.1M solution) was added in three lots over a period of 30 min and held overnight. Coupling was repeated with fresh benzotriazole ester and after the second coupling the resin was acetylated with 10 equivalents of 1-acetylimidazole for 1 hr. 50% TFA-CH$_2$Cl$_2$ was used for Boc deprotection (1% 2-mercaptoethanol was added in TFA-CH$_2$Cl$_2$ after coupling D-Trp). The next two amino acids, Leu and Arg, were coupled as the dipeptide Boc-Leu-Arg (Tos) benzotriazole ester (preformed in preparation 6) at pH 6.5. All other amino acids were coupled individually as their preformed benzotriazole esters. After Boc deprotection, the neutralization step was substituted by isopropanol (80% in CH$_2$Cl$_2$) washes. Coupling of Boc-Leu-Arg(Tos)-OBt was performed using 3×3 equivalents for 24 hr each coupling without the addition of base. Before the addition of the remainder of the amino acid active esters, the pH of the resin suspension was brought to the pH of CH$_2$Cl$_2$-DMF (9:1 v/v); (about 6.5), by adding 0.1M solution of DIEA in CH$_2$Cl$_2$. About one equivalent of DIEA was required each time. After the addition of active ester 1.2 equivalents of DIEA were added (as 0.1M solution) in three lots over a period of 30 min. Couplings were monitored by Kaiser test (E. Kaiser, *Anal Biochem* (1970) 34: 595) and double coupling was performed whenever necessary. The deprotection and coupling cycle consisted of the following operations:

| | |
|---|---|
| CH$_2$Cl$_2$ | 3 × 1 min |
| 50% TFA-CH$_2$Cl$_2$ prewash | 5 min |
| 50% TFA-CH$_2$Cl$_2$ | 25 min |
| CH$_2$Cl$_2$ | 6 × 1 min |
| 80% Isopropanol - CH$_2$Cl$_2$ | 3 × 1 min |
| CH$_2$Cl$_2$ | 3 × 1 min |
| pH adjustment with 1 eq. DIEA-CH$_2$Cl$_2$ (0.1 M solution) | |
| Coupling; threefold excess of preformed benzotriazole active ester | Monitored by Kaiser test |
| 1.2 eq. DIEA-CH$_2$Cl$_2$ (0.1 M solution) in three lots over a period of 30 min. | |
| CH$_2$Cl$_2$ | 3 × 1 min |

After completion of the synthesis, peptide was cleaved from the resin with anhydrous liquid HF (containing 10% anisole and 1% 2-mercaptoethanol) at 4° C. for 1 hr. Resin was washed thrice with ether and the peptide was extracted into concentrated acetic acid (20 mL). The acid extract was diluted and lyophilized. Crude peptide was subjected to gel filtration on a Sephadex G-15 column, eluting with 40% acetic acid. Peptide was then purified on HPLC using preparative Vydac C$_{18}$ column using 29% CH$_3$CN in H$_2$O+0.05% TFA as eluent to obtain 277 mg of product as a white powder. Overall yield 20% on the basis of substitution on the resin.

The peptide analogs were analyzed for purity by analytical HPLC and TLC (solvent systems:
n-BuOH:HAc:H$_2$O:EtOAc, 1:1:1:1 v/v;
n-BuOH:HAc:pyridine:H$_2$O 30:6:20:24 v/v;
n-BuOH:HAc:H$_2$O 4:1:1 v/v; and n-BuOH:HAc:H$_2$O 4:1:5 v/v) and amino acid analysis. Presence of ketomethylene group was detected by $^{13}$C NMR.

EXAMPLE 2

Synthesis of Ac-[D-Phe[1], D-P-Cl-Phe[2], D-Trp[3], D-Arg[6]] Pro-KmGly[9,10] using Fmoc protection and reactions 2.9–2.13

Synthesis of this peptide was carried out in a Peptider (Peninsula Laboratories) synthesis unit using Fmoc amino acids and the benzhydrylaminopolystyrene—2% divinylbenzene resin. The first two residues were coupled as the dipeptide Fmoc-Pro-Kam-Gly, hydroxybenzotriazole active ester 17 prepared in Preparation 10 above. The solution of 17 was added to the resin followed by the addition of one equivalent of diisopropylethylamine and coupled overnight. Coupling was repeated with additional fresh benzotriazole ester. After the second coupling, Kaiser test was slightly positive and, therefore, peptide resin 18 was acetylated using reaction 1.7.

Preformed Fmoc amino acid symmetrical anhydrides (Wieland et al, *Justus Liebigs Ann Chem* (1973) 10: 1595) in threefold excess were used for each coupling which was carried out by reaction 2.11. Completeness of coupling was checked by Kaiser test. Diisopropylethylamine was added before the last 15 minutes of coupling. In most cases coupling was complete in 1 hr. In the case of Pro, L-Arg, D-Arg, and Tyr, coupling took longer and a second coupling was used. 50% piperidine in $CH_2Cl_2$ was used for Fmoc deprotection in accord with reaction 2.10. The incorporation of an amino acid residue within the growing peptide chain consisted of the following operations:

| | |
|---|---|
| $CH_2Cl_2$ | 3 × 1 min |
| 50% Piperidine in $CH_2Cl_2$ | 5 min |
| 50% Piperidine in $CH_2Cl_2$ | 25 min |
| $CH_2Cl_2$ | 3 × 1 min |
| DMF | 3 × 1 min |
| $H_2O$—Dioxane (1:2) | 3 × 1 min |
| DMF | 3 × 1 min |
| $CH_2Cl_2$ | 3 × 1 min |
| Coupling, threefold excess of preformed Fmoc-amino acid anhydride in $CH_2Cl_2$: DMF (9:1 v/v) | monitored by Kaiser test |
| $CH_2Cl_2$ | 3 × 1 min |
| DMF | 3 × 1 min |
| 80% Isopropanol in $CH_2Cl_2$ | 3 × 1 min |
| $CH_2Cl_2$ | 3 × 1 min |

After the last coupling, the Fmoc group was removed and the peptide resin was acetylated for 1 hr with $Ac_2O$:pyridine:benzene (1:3:3 v/v). The acetylated peptide-resin was washed with $CH_2Cl_2$ 3×, 80% isopropanol-$CH_2Cl_2$ 3× and dried under vacuum. Resin was cleaved in reaction 2.13 with anhydrous liquid HF containing 10% anisole and 1% 2-mercaptoethanol, at 4° C. for 45 min in a type I hydrofluoric acid apparatus from Protein Research Foundation. After the reaction HF was completely evaporated under vacuum. The resin was washed with anhydrous ether 3× to remove anisole. The peptide was extracted into 50% acetic acid (25 mL). The extract was diluted with water and lyophilized. Crude peptide was subjected to gel filtration on Sephadex G-15 (2.5×83 cm) using 40% acetic acid as eluent. Peptide was then purified by partition chromatography on Sephadex G-50 (Fine) using the solvent system n-BuOH:HAc:$H_2O$ 4:1:5 v/v. It was repartitioned on Sephadex G-25 (Fine) using the same solvent system to obtain 80 mg of the product as a white powder, overall yield 14.3% based on the substitution on the resin as monitored by the picrate method of Hodges and Merrifield, *Anal Biochem* (1975) 65: 241.

The material of Example 2, (Material II) prepared using Fmoc protection, appeared to be purer than the material of Example 1 (Material I). The material of Example 1, when studied by HPLC, appeared to have an unseparable shoulder appearing just before the desired primary compound. The $^{13}C$-NMR of the material of Example 1 showed two lines in the ketone carbonyl region in the ratio of 2:3. Material I of Example 1 showed lower antiovulatory activity than did Material II of Example 2.

Samples of the products of Examples 1 and 2 as well as a sample of the comparable non-Km modified LHRH analog were hydrolyzed to their constituent amino acids and the mole ratios of these acids determined. The results were given in Table 5 and show that the products of Examples 1 and 2 are the desired materials.

TABLE 5

| | Amino Acid Ratios Found[a] | | | | | | |
|---|---|---|---|---|---|---|---|
| Compound | Phe | Ser | Tyr | Leu | Arg[e] | Pro | Gly |
| Std[b] | 0.98 | 0.78 | 1.01 | 1.00 | 2.03 | 0.99 | 1.00 |
| II[c] | 0.99 | 0.81 | 1.02 | 0.99 | 1.63 | | |
| I[d] | 1.03 | 0.88 | 1.01 | 0.95 | 1.46 | | |

[a]Hydrolysis was conducted in 6N HCl at 110° C. for 24 hours. Amino acid ratios were calculated by averaging the values obtained for amino acids other than Serine, which is partially destroyed during hydrolysis. Tryptophan is totally destroyed during hydrolysis.
[b]Standard LHRH antagonist Ac—D-Phe[1], D-pCl—Phe[2], D-Trp[3], D-Arg[6]]LHRH prepared by Fmoc-protected solid phase procedure as described by Chang et al in *Int J Pept Protein Res* 15: (1980) 485.
[c]Ketomethylene LHRH antagonist analog from Fmoc synthesis of Example 2.
[d]Ketomethylene LHRH antagonist analog from Boc synthesis of Example 1.
[e]Amino acid ratios of 2a and 2b contained a reduced amount of Arg, since it has been reported that amino acids attached to the amino side of a ketomethylene dipeptide are poorly cleaved. (D. Hudson et al, U.S. Pat. No. Re30,731, 1 September 1981.)

EXAMPLE 3

Preparation of LHRH agonist

Example 1 was repeated with the change that the amino acid residues at positions 1–8 were varied. This gave the LHRH agonist [D-Nal(2)[6], Pro[9]-KmGly[10]] LHRH (Material III).

EXAMPLE 4

Preparation of Pro[9]-$H_2$KmGly[10] materials

Example 1 was repeated with the change that in place of Boc-Pro-KmGly the R and S benzylated Boc-Pro-Bzl$H_2$KmGly intermediates 27R and 27S were used. (These materials were prepared in preparations 11–13 above.)

These individual isomeric materials were incorporated into the LHRH analog to yield:
[AC-D-Phe[1], D-p-Cl-Phe[2], D-Trp[3], D-Arg[6], Pro[9]-$H_2$Km(R)Gly[10]] LHRH (Material IVR) and
[Ac-D-Phe[1], D-p-Cl-Phe[2], D-Trp[3], D-Arg[6], Pro[9]-$H_2$Km(S)Gly[10]] LHRH (Material IVS)

EXAMPLE 5

Preparation of [Pro[9]-KmGly[10]] LHRH

The processes of Example 1 and Example 2 can be repeated with the changes that after coupling the Pro[9] and KmGly[10] units to the polymer, the remaining amino acid residues are varied to give Glu-His-Trp-Ser-Tyr-Gly-Leu and Arg in positions 1 through 8, respectively, so as to obtain by such process [Pro[9]-KmGly[10]] LHRH. Similarly, if the Pro[9]-$H_2$KmGly[10] units are employed, [Pro[9]-$H_2$KmGly[10]] LHRH is obtained.

Biological Activity

The antiovulatory activity of the materials I, II, II, IVS, IVR of examples 1, 2, 3, and 4 were determined by tests carried out at the Contraceptive Development Branch of the National NICHD at the National Institutes of Health and compared with the activity of the standard LHRH analog "Std" described in Table 5.

The antiovulatory activities of the various LHRH analogs of Examples 1, 2, 3, and 4 are shown in Tables 6 and 7. Insertion of a ketomethylene between Pro-Gly in the model LHRH antagonist "Std" yielded LHRH antagonist analogs I and II that are more than twice as potent when given by oral administration as is "Std" itself. Also, it should be noted that the oral-to-sc $ED_{100}$ ratio for Std is, as expected, >1000, whereas that of I and II is ~100. The amide linkage between Pro-Gly does seem to be important for LHRH receptor binding since a comparison of Std and I and II in an LHRH pituitary receptor binding assay found that I and II bind one-sixth as well as Std. This result is confirmed by the fact that I and II have one-fifth the sc antiovulatory activity of Std. Whether the improved oral activity of I or II compared to Std is caused by its greater stability to peptidase degradation or its increased absorption due to it more lipophilic character is not known.

TABLE 6

Antiovulatory Activity of LHRH Analogs

| | Antiovulatory Activity[a] (Rats ovulating/rats tested) | |
|---|---|---|
| Dose (mg/rat) | Std | II |
| 0.005 sc | 2/10 | 0 |
| 0.01 sc | 0/10 | 8/10 |
| 0.025 sc | — | 1/10 |
| 0.05 sc | — | 0/10 |
| 2.5 po | — | 1/6 |
| 5.0 po | 5/10 | — |

[a]The peptides are given at 12:00 noon on the day of proestrus. This data was obtained from the Contraceptive Development Branch of NICHD at the National Institutes of Health. The procedure of Rivier et al was followed for rat antiovulatory testing. (See Contraceptives, Harper & Row, Philadelphia, 1981, pp. 13–23.)

The hydroxydimethylene LHRH antagonist analog of the invention IV has sc antiovulatory activity similar to that of the ketomethylene-containing antagonist I and II. However, the oral activity of IV is less than that of I or II at the highest dose tested, thus suggesting that it is the increased lipophilic character of I and II that is most important for their improved oral activity compared to Std. The hydroxydimethylene LHRH antagonist analog IV, with R stereochemistry at the hydroxyl carbon, is much less potent than the S isomer. This further indicates that the peptide backbone between Pro$^9$ and Gly$^{10}$ is involved in some important interactions—either intramolecularly or intermolecularly—with its receptor.

The agonist analog III has approximately one-half the sc pregnancy-inhibiting activity of [D-Nal(2)$^6$] LHRH. Peptide III did not produce significant inhibition of pregnancy at an oral dose that was 250 times its sc ED$_{100}$ dose. This is not too surprising since III still contains at least five amide bonds that are not protected from peptidase cleavage.

What is claimed is:

1. A compound of the formula R$^1$-R$^2$-R$^3$-Tyr$^5$-R$^6$-R$^7$-Arg$^8$-Pro$^9$-KmGly$^{10}$ wherein:
R$^1$ is an aminoacyl residue selected from the group consisting of: L-pGlu, D-pGlu, Ac-D-Pro, Ac-L-Pro, Ac-L-Trp, substituted D-Ala, Ac-D-Phe, Ac-p-halo-D-Phe, D-Nal, Ac-D-Nal; Gly, D-Ala, L-Ala, D-Trp, and D-Phe with and without benzoylalkanoyl, benzoyl, alkanoyl, acyl, and HOOC-(CH$_2$)$_n$-CO-substituents wherein n is 2–6; and Ac-p-halo-D-Pro;
R$^2$ is an aminoacyl residue selected from the group consisting of: L-His, halo-D-Phe, NO$_2$-D-Phe, dihalo-D-Phe, D-Phe, L-Phe, D-Ala, substituted D-Ala, substituted D-Phe, and diphenyl-Gly;
R$^3$ is an aminoacyl residue selected from the group consisting of: L-Trp, D-Trp, D-Phe, L-Phe, substituted D-Phe, substituted D-Ala, and D-Nal;
R$^6$ is a aminoacyl residue selected from the group consisting of: L-Gly and D-aminoacyl residues; and
R$^7$ is an aminoacyl residue selected from the group consisting of Leu, and N-Me-Leu.

2. The compound of claim 4 having the structure: [Pro$^9$-KmGly$^{10}$] LHRH.

3. A compound having the structure [R$^6$, Pro$^9$-KmGly$^{10}$] LHRH wherein R$^6$ is selected from a D-isomer of an α-amino acid selected from Trp, Ala, Phe, Lys, Pro, Met, Leu, Glu, Asn, Arg, Tyr, Cys, His, Chg, Nva, Orn, Thr, Abu, Phg, Ile, Asp, Nle, Val, t-Bu-Ser, Nal, m-Bzl-His, and Cha.

4. The compound of claim 1 having the structure: [D-Trp$^6$, N-MeLeu$^7$, Pro$^9$-KmGly$^{10}$] LHRH.

5. The compound of claim 1 having the structure: [Ac-D-amino acid$^1$, D-Phe$^2$, D-Trp$^{3,6}$, Pro$^9$-KmGly$^{10}$] LHRH.

6. The compound of claim 1 having the structure: [Ac-D-Phe$^1$, D-pCl-Phe$^2$, D-Trp$^3$, D-Arg$^6$ Pro$^9$-KmGly$^{10}$] LHRH.

7. The compound of claim 1 having the structure: [Ac-D-Nal(2)$^1$, D-p-Cl-Phe$^2$, D-Trp, D-hArg(Et$_2$)$^6$, Pro$^9$-KmGly$^{10}$] LHRH.

8. A compound of formula R$^1$-R$^2$-R$^3$-Ser$^4$-Tyr$^5$-R$^6$-R$^7$-Arg$^8$-Pro$^9$-H$_2$KmGly$^{10}$ wherein:
R$^1$ is an aminoacyl residue selected from the group consisting of: L-pGlu, D-pGlu, Ac-D-Pro, Ac-L-Pro, Ac-L-Trp, substituted D-Ala, Ac-D-Phe, Ac-p-halo-D-Phe, D-Nal, Ac-D-Nal; Gly, D-Ala, L-Ala, D-

TABLE 7

| | Antiovulatory Activity (rats ovulating or pregnant/rats tested) | | | | | | | | | | |
|---|---|---|---|---|---|---|---|---|---|---|---|
| | | Subcutaneous (mg/rat) | | | | | | | Oral (mg/rat) | | |
| Compound | No. | 0.001 | 0.0025 | 0.005 | 0.01 | 0.025 | 0.05 | 0.1 | 0.25 | 2.5 | 5.0 |
| [Ac—D-Phe$^1$, D-p-Cl—Phe$^2$, D-Trp$^3$, D-Arg$^6$] LHRH | Std | | | 2/10 | 0/10 | | | | | | 5/10 |
| [Ac—D-Phe$^1$, D-p-Cl—Phe$^2$, D-Trp$^3$, D-Arg$^6$,Pro$^9$—KmGly$^{10}$] LHRH | II | | | 8/10 | 1/10 | 0/10 | 0/10 | | | 1/6 | |
| [Ac—D-Phe$^1$, D-p-Cl—Phe$^2$, D-Trp$^3$, D-Arg$^6$, Pro$^9$—H$_2$Km(S)Gly$^{10}$] LHRH | IVS | | | | 2/10 | | | | | 7/10 | |
| [Ac—D-Phe$^1$, D-p-Cl—Phe$^2$, D-Trp$^3$, D-Arg$^6$, Pro$^9$—H$_2$Km(R)Gly$^{10}$] LHRH | IVR | | | | 9/10 | | 8/10 | | | | |
| [D-Nal(2)$^6$, Pro$^9$—KmGly$^{10}$]LHRH | III | 1/10 | 0/10 | | | | | | 9/10 | | |

Trp, and D-Phe with and without benzoylalkanoyl, benzoyl, alkanoyl, acyl, and HOOC-(Ch$_2$)$_n$-CO-substituents wherein n is 2–6; and Ac-p-halo-D-Pro;

R$^2$ is an aminoacyl residue selected from the group consisting of: s L-His, halo-D-Phe, No$_2$-D-Phe, dihalo-D-Phe, D-Phe, L-Phe, D-Ala, substituted D-Ala, substituted D-Phe, and diphenyl-Gly;

R$^3$ is an aminoacyl residue selected from the group consisting of: L-Trp, D-Trp, D-Phe, L-Phe, substituted D-Phe, substituted D-Ala, and D-Nal;

R$^6$ is a aminoacyl residue selected from the group consisting of: L-Gly and D-aminoacyl residues; and R$^7$ is an aminoacyl residue selected from the group consisting of Leus, and N-Me-Leu.

9. The compound of claim 8 having the structure: [Pro$^9$-H$_2$KmGly$^{10}$] LHRH.

10. A compound having the structure [R$^6$, Pro$^9$-H$_2$KmGly$^{10}$] LHRH wherein R$^6$ is selected from a D-isomer of an α-amino acid selected from Trp, Ala, Phe, Lys, Pro, Met, Leu, Glu, Asn, Arg, Tyr, Cys, His, Chg, Nva, Orn, Thr, Abu, Phg, Ile, Asp, Nle, Val, t-Bu-Ser, Nal, m-Bzl-His, and Cha.

11. The compound of claim 8 having the structure: [D-Trp$^6$, N-MeLeu$^7$, Pro$^9$-H$_2$KmGly$^{10}$] LHRH.

12. The LHRH analog of claim 8 having the structure:

[Ac-D-amino acid$^1$, D-Phe$^2$, D-Trp$^{3,6}$, Pro$^9$-H$_2$KmGly$^{10}$] LHRH.

13. The LHRH analog of claim 8 having the structure:

[Ac-D-Phe$^1$, D-pCl-Phe$^2$, D-Trp$^3$, D-Arg$^6$ Pro$^9$-H$_2$KmGly$^{10}$] LHRH.

14. The LHRH analog of claim 8 having the structure:

[Ac-D-Nal(2)$^1$, D-p-Cl-Phe$^2$, D-Trp, D-hArg(Et$_2$)$^6$, Pro$^9$-H$_2$KmGly$^{10}$] LHRH.

15. An orally effective LHRH pharmaceutical preparation comprising an orally effective amount of an a compound of claim 1 in admixture with a pharmaceutically acceptable carrier.

16. A method for producing an LHRH effect in a mammal which comprises orally administering to said mammal an effective dose of the pharmaceutical preparation of claim 15.

17. An orally effective LHRH pharmaceutical preparation comprising an orally effective amount of a compound of claim 8 in admixture with a pharmaceutically acceptable carrier.

18. A method for producing an LHRH effect in a mammal which comprises orally administering to said mammal an effective dose of the pharmaceutical preparation of claim 17.

* * * * *